US011653835B2

(12) United States Patent
Bodenschatz et al.

(10) Patent No.: US 11,653,835 B2
(45) Date of Patent: May 23, 2023

(54) DUAL MODE BIOPHOTONIC IMAGING SYSTEMS AND THEIR APPLICATIONS FOR DETECTION OF EPITHELIAL DYSPLASIA IN VIVO

(71) Applicant: PROVINCIAL HEALTH SERVICES AUTHORITY, Vancouver (CA)

(72) Inventors: Nico Bodenschatz, Vancouver (CA); Calum E. MacAulay, Vancouver (CA)

(73) Assignee: Provincial Health Services Authority, Vancouver (CA)

( * ) Notice: Subject to any disclaimer, the term of this patent is extended or adjusted under 35 U.S.C. 154(b) by 1024 days.

(21) Appl. No.: 16/348,244

(22) PCT Filed: Nov. 21, 2017

(86) PCT No.: PCT/CA2017/051393
§ 371 (c)(1),
(2) Date: May 8, 2019

(87) PCT Pub. No.: WO2018/094518
PCT Pub. Date: May 31, 2018

(65) Prior Publication Data
US 2019/0269333 A1    Sep. 5, 2019

Related U.S. Application Data

(60) Provisional application No. 62/425,518, filed on Nov. 22, 2016.

(51) Int. Cl.
*A61B 5/00* (2006.01)
*A61B 1/303* (2006.01)
(Continued)

(52) U.S. Cl.
CPC ............ *A61B 5/0071* (2013.01); *A61B 1/303* (2013.01); *A61B 5/00* (2013.01); *A61B 5/0035* (2013.01);
(Continued)

(58) Field of Classification Search
CPC .... A61B 5/0071; A61B 5/0035; A61B 8/0858
See application file for complete search history.

(56) References Cited

U.S. PATENT DOCUMENTS

2015/0087902 A1   3/2015   Mertz et al.
2017/0202633 A1   7/2017   Liu

FOREIGN PATENT DOCUMENTS

WO    WO-2017185161 A1 * 11/2017 ............. G01B 11/24

OTHER PUBLICATIONS

Schiffman, M. et al., "Human papillomavirus and cervical cancer", Lancet. 370: 890-907 (2007).
(Continued)

*Primary Examiner* — Rochelle D Turchen
(74) *Attorney, Agent, or Firm* — Todd A. Rattray; Oyen Wiggs Green & Mutala LLP

(57) ABSTRACT

A system provides combined diffuse optical microscopy (DOM) and fluorescence endomicroscopy (FE). The system may use a single light source which generates structured illumination for both modalities. FE and DOM images may be displayed for qualitative assessment. Quantitative assessments may be based on both FE and DOM images. The quantitative assessments may be applied to characterize tissues. Some embodiments provide multi-spectral DOM.

19 Claims, 12 Drawing Sheets

(51) Int. Cl.
  *A61B 5/06*  (2006.01)
  *A61B 8/08*  (2006.01)
(52) U.S. Cl.
  CPC .............. *A61B 5/06* (2013.01); *A61B 5/4325* (2013.01); *A61B 8/0858* (2013.01)

(56) References Cited

OTHER PUBLICATIONS

Weber, C.R. et al., "Model-based analysis of reflectance and fluorescence spectra for in vivo detection of cervical dysplasia and cancer", J. Biomed. Opt. 13(6):064016 (Nov./Dec. 2008).
Bodenschatz, N. et al., "Diffuse optical microscopy for quantification of depth-dependent epithelial backscattering in the cervix" m J. Biomed. Opt. 21(6), 066001 (Jun. 2016).
Bozinovic, N. et al., "Fluorescence endomicroscopy with structured illumination", Opt. Express 16(11), 8016-8025 (2008).
Schlosser, C. et al., "Fluorescence confocal endomicroscopy of the cervix: pilot study on the potential and limitations for clinical implementation", J. Biomed. Opt. 21(12), 126011 (Dec. 2016).

* cited by examiner

BS  CIN 1  CIN 2  CIN 3  CANCER

DUAL MODE BIOPHOTONIC IMAGING SYSTEMS AND THEIR APPLICATIONS FOR DETECTION OF EPITHELIAL DYSPLASIA IN VIVO

CROSS-REFERENCE TO RELATED APPLICATION

This application claims priority from U.S. patent application 62/425,518 filed Nov. 22, 2016. For purposes of the United States, this application claims the benefit under 35 U.S.C. § 119 of application No. 62/425,518 filed Nov. 22, 2016, and entitled DUAL MODE BIOPHOTONIC IMAGING FOR DETECTION OF EPITHELIAL DYSPLASIA IN VIVO which is hereby incorporated herein by reference for all purposes.

FIELD

This invention relates to systems for optical imaging of tissues in vivo and to applications of such systems for detection and assessment of cancers and pre-cancers.

BACKGROUND

It has been demonstrated that effective screening programs can markedly reduce the incidence of cancers that require treatment. For example, the incidence of cervical cancer is significantly lower in countries that have implemented screening programs for cervical cancer than in countries which lack screening programs.

Early detection of cancers or precancers that are at risk of developing into cancers can significantly improve outcomes for patients. Both cancerous and precancerous tissues are associated with microstructural alterations in comparison to normal tissues. Such changes in cellular differentiation and sub-cellular architecture are often microscopically observable well before tissues develop into invasive cancer. An effective non-invasive optical modality for early cancer detection and screening would be of great benefit.

Current tools for early cancer screening often suffer from low sensitivities (Pap smear screening of the cervix has a sensitivity of only 53%). This frequently necessitates invasive tissue biopsies and subsequent histopathologic assessment. In vivo detection of epithelial dysplasia could help to overcome the need for such biopsies thus reducing treatment time and costs.

Some existing systems that could be used to screen for cancers or precancers suffer from low resolution owing to the lack of histology-like tissue slicing and the inability to resolve tissue structure beyond the first few cell layers and/or impractically high costs.

There is a need for improved (more sensitive, more selective, and/or lower cost) systems useful for screening for cancers in epithelial tissues such as tissues of the cervix and the oral cavity. There is a particular need for such systems that can be provided at low cost to enable widespread screening even in low resource settings.

SUMMARY

This invention has a number of aspects. These include, without limitation:
  systems operable for combined fluorescence endoscopy imaging and diffuse optical microscopy imaging;
  systems operable for combined multi-spectral imaging and diffuse optical microscopy imaging;
  systems and methods for processing data and/or images from diffuse optical microscopy imaging to yield measures of dysplasia and/or measures of cancer risk;
  methods for combined multi-spectral imaging and diffuse optical microscopy imaging;
  methods for combined multi-spectral imaging and diffuse optical microscopy imaging;
  methods for enhancing fluorescence endoscopy images with data from co-registered diffuse optical microscopy images;
  methods for enhancing fluorescence endoscopy images with data from co-registered multi-spectral diffuse optical microscopy images;
  methods for multi-spectral diffuse optical microscopy; and
  methods and systems for screening and/or characterizing epithelium tissues.

Dual-mode endomicroscopy is a diagnostic tool for early cancer detection. It combines the high resolution nuclear tissue contrast of fluorescence endomicroscopy with quantified depth-dependent epithelial backscattering as obtained by diffuse optical microscopy.

One aspect of the present invention provides a method and apparatus for performing dual mode biophotonic imaging for detection of epithelial dysplasia in vivo. In some applications, the present systems may be used for detection of cervical cancer. In alternative applications, oral cancer or other epithelial cancers are detected. In one embodiment a preferred wavelength of about 450 nm is used for the light source. In alternative embodiments, a wavelength ranging from 300 nm to 600 nm may be used.

Another aspect of the invention provides systems for combined diffuse optical microscopy (DOM) and fluorescence endomicroscopy (FE). Such systems may comprise: a light source; a spatial light modulator illuminated by the light source and operative to spatially modulate the light from the light source to provide a structured illumination pattern; an optical system arranged to demagnify the structured illumination pattern and to direct the structured illumination pattern into a fiber bundle terminating at a probe tip; a first camera optically connected to receive light backscattered into the probe tip; a second camera optically connected to receive fluorescence light incident on the probe tip; a light filtering optical element in a light path between the probe tip and the second camera, the light filtering optical element operative to block light other than the fluorescence light; and a controller. The controller comprises an image processing system connected to receive image data from the first camera and the second camera and to process the image data to yield a DOM image based on images from the first camera and a FE image based on images from the second camera, the FE image co-registered with the DOM image.

The light source may comprise a blue light source such as a laser or light emitting diode. In some embodiments the light source emits light having a wavelength of 450 nm±10 nm. In some embodiments the light filtering optical element comprises a dichroic mirror. The light filtering element may pass green light such as optical radiation having wavelengths corresponding to fluorescent emissions of acriflavine hydrochloride (AH) to the second camera.

The structured light pattern is spatially periodic with a spatial frequency in at least one direction. The controller is operative to control the spatial light modulator to modulate the light from the light source according to the structured light pattern and to trigger the first and second cameras to capture images while the spatial light modulator is modulating the light from the light source according to the structured light pattern. The first and second cameras may be triggered simultaneously.

In some embodiments the controller is operative to apply phase shifts to the structured light pattern in the at least one direction and to, in a sequence, control the spatial light modulator to modulate the light from the light source according to the structured light pattern with different phase shifts applied, and to trigger the first and second cameras to capture images while the spatial light modulator is modulating the light from the light source according to the structured light pattern with each of the applied phase shifts.

The controller may combine captured images for each of the phase shifts. Such combination may include one or more of:
  computing differences between pairs of the captured images and summing the differences;
  computing the value $$R = A\sqrt{(X_1-X_2)^2 + (X_2-X_3)^2 + (X_3-X_1)^2}$$

where $X_1$, $X_2$ and $X_3$ are captured images for three different phase shifts and A is a constant;
  computing an average of the captured images.
Different combinations may be performed for images from the first and second cameras.

The controller may be operative to alter the spatial frequency of the structured light pattern and to control the spatial light modulator to modulate the light from the light source according to the structured light pattern with one of plural different spatial frequencies, and to trigger the first and second cameras to capture images while the spatial light modulator is modulating the light from the light source according to the structured light pattern with each of the plural spatial frequencies.

The controller may be operative to apply phase shifts to the structured light pattern in the at least one direction and to, in a sequence, control the spatial light modulator to modulate the light from the light source according to the structured light pattern with different phase shifts applied, and to trigger the first and second cameras to capture images while the spatial light modulator is modulating the light from the light source according to the structured light pattern with each of the applied phase shifts. This may be done for one or more different spatial frequencies.

In some embodiments the controller is configured to determine a ratio (R) of images from the first camera corresponding to different ones of the plural spatial frequencies.

In some embodiments the structured light pattern has a spatial frequency is in the range of 2 $mm^{-1}$ to 20 $mm^{-1}$.

In some embodiments the controller is configured to process the images from the second camera to calculate a measure of nuclear-to-cytoplasmic ratio.

In some embodiments the controller is configured to process the images from the second camera to calculate a measure of nuclear-to-cytoplasmic ratio (NCR) and to characterize tissues imaged by the system based on a discriminant function having the NCR and R as inputs, where R is a ratio of reflectance at different spatial frequencies of the structured illumination and/or at different wavelength ranges of light.

In some embodiments the first camera comprises a multispectral camera and the system comprises a second light source operable to emit light in a range of frequencies that is broader than the spectrum of the first light source. The second light source may, for example, be operable to emit white light. In such embodiments the controller may optionally be configured to operate the light source and the second light source at different times and to trigger the second camera while the first light source is being operated and to trigger the first camera while the second light source is being operated.

Systems as described herein may include a display or other human perceptible output device. A system may be configured to display on the display a FE image generated from images captured by the second camera and a DOM image generated from images captured by the first camera and/or a combined FE and DOM image.

In some embodiments the controller is configured to control the spatial modulation provided by the spatial light modulator to project structured illumination having plural different spatial frequencies; control the first camera to capture one or more images corresponding to the structured illumination of each of the plural spatial frequencies, and process the captured images to calculate a ratio of reflectance for one or more pairs of the plural spatial frequencies. In such embodiments the controller is optionally configured to calculate the ratio of reflectance on a pixel-by pixel basis and generate a pseudo colour image with colour set according to the ratio of reflectance.

In some embodiments the controller is configured to control the spatial modulation provided by the spatial light modulator to project structured illumination having plural different spatial frequencies, control the first camera to capture one or more images corresponding to the structured illumination of each of the plural spatial frequencies, and process the captured images to generate a combined pseudo colour image wherein different colour channels of the pseudo colour image are respectively set based on captured images corresponding to different ones of the plural spatial frequencies such that changes with position in ratios of the reflectance corresponding to different spatial frequencies correspond to colour shifts in the pseudo colour image.

In some embodiments the first camera is a multi-spectral camera and the controller is configured to control the spatial modulation provided by the spatial light modulator to project structured illumination having one or more spatial frequencies, control the first camera to capture one or more images corresponding to the structured illumination and process the captured images to generate a pseudo colour image wherein different colour channels of the pseudo colour image are respectively set based on different spectral channels of the multispectral first camera.

In some embodiments the first camera is a multispectral camera, the controller is configured to control the spatial modulation provided by the spatial light modulator to project structured illumination having plural different spatial frequencies, control the first camera to capture one or more images corresponding to the structured illumination of each of the plural spatial frequencies, and process the captured images to generate a combined pseudo colour image wherein different colour channels of the pseudo colour image are respectively set based on captured images corresponding to different ones of the plural spatial frequencies and/or different spectral channels of the multispectral camera such that changes with position in ratios of the reflectance corresponding to different spatial frequencies and/or different spectral channels correspond to colour shifts in the pseudo colour image.

In some embodiments the controller is configured to determine a depth of an epithelial tissue adjacent to the probe tip and to control the spatial modulation provided by the spatial light modulator based at least in part on the depth. For example, spatial frequency(ies) of the structured illumination may be selected based on the epithelium thickness. The thickness may be detected by any one or more of:

receiving user input by way of the user interface;
processing images captured by the first camera;
operating a depth transducer such as an ultrasound transducer located at the probe tip.

In some embodiments the first camera is a multispectral camera. In some implementations the first camera has at least four spectral bands. The spectral bands may, for example, comprise bands that detect light in the wavelength ranges of 400-410 nm, 540-560 nm, and 560-570 nm and/or the wavelength ranges of 400-410 nm, 560-570 nm, and 570-585 nm. The spectral bands may, for example, comprise bands that are centered at one or more of approximately 405 nm, 545 nm, 565 nm and 585 nm.

Other aspects of the invention provide methods. The following are non-limiting examples of such methods. Other examples are provided in the Description.

One method aspect provides a method for characterizing epithelium tissue. The method comprises: obtaining one or more first images of the tissue while the tissue is illuminated by a first structured light pattern having a first spatial frequency; obtaining one or more second images of the tissue while the tissue is illuminated by a second structured light pattern having a second spatial frequency; processing the first image and the second image to obtain a ratio of reflectance of the tissue under the first and second structured light patterns and characterizing the tissue based at least in part on the ratio. The ratio may be computed on a pixel-by-pixel basis. For some applications a representative value of the ratio (e.g. a mean or average or median) is determined for a region.

The method may include determining a thickness of the tissue and selecting at least one of the first and second spatial frequencies or some other attribute of one or more of the spatial illumination patterns based on the thickness.

Some embodiments further comprise obtaining fluorescence images of the tissue and characterizing the tissue based at least in part on the fluorescence images. The fluorescence images may optionally be obtained simultaneously with at least one of the first and second images. For example some embodiments process the fluorescence images to determine a CNR and base the tissue characterization at least in part on the CNR. Some embodiments perform characterizing the tissue in a manner comprising computing a discriminant function that takes the ratio and the CNR as inputs.

Another example method aspect provides a method for characterizing tissue comprising: obtaining one or more first images of the tissue while the tissue is illuminated by a first structure illumination pattern of light of a first wavelength, the first structured illumination pattern characterized by light of a first spatial frequency; simultaneously with obtaining the first images obtaining second images of the tissue at a second wavelength different from the first wavelength; and, one or both of processing the first image to yield a diffuse optical microscopy image and processing the second images to yield a fluorescence endoscopy image; and processing the first and second images to yield a combined fluorescence endoscopy and diffuse optical microscopy image.

The invention is not limited to any of the above aspects. Further aspects and example embodiments are illustrated in the accompanying drawings and/or described in the following description.

BRIEF DESCRIPTION OF THE DRAWINGS

The accompanying drawings illustrate non-limiting example embodiments of the invention.

DETAILED DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive sense.

The present invention provides optical systems and associated methods useful for visualizing pathologic microstructural features in vivo. These systems and methods are applicable for both cancer screening and on-site tumor margin assessment.

The majority of cancers originate from epithelial tissue. Triggers such as infection by human papillomavirus (HPV) can initiate a progression toward cancer. During early precancerous development in the squamous epithelium, structural phenotypic changes are often initially observable in cells and cell nuclei adjacent to the epithelial basement membrane. These alterations are frequently denoted as "mild" dysplasia in their earliest stage. If mild dysplasia transforms further, abnormal cells and cell packing alterations become more prominent also in the middle and upper parts of the epithelium and are termed "moderate" and "severe" dysplasia, respectively. Throughout this precancerous progression from mild to moderate to severe degree, the altered tissue is increasingly likely to develop into carcinoma in situ (CIS) and eventually into invasive cancer.

Figure 1:
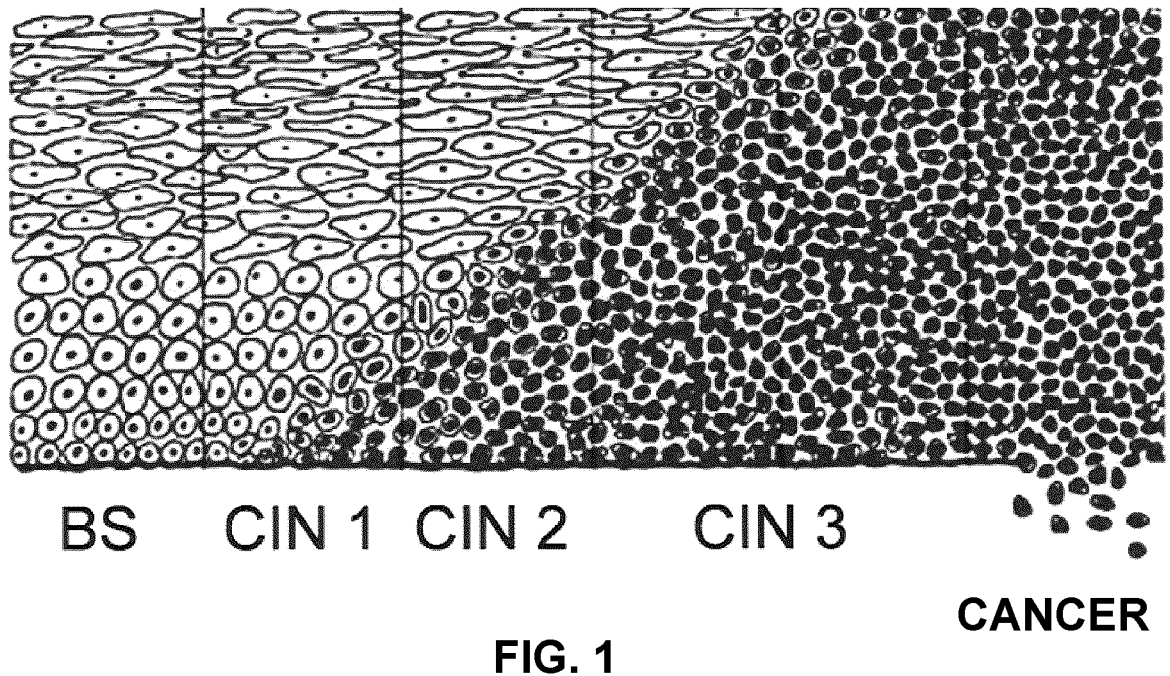
FIG. 1 is a schematic representation showing changes that occur as an epithelial tissue progresses toward invasive cancer.

FIG. 1 shows schematically, from left to right, changes that occur as an epithelial tissue, for example normal squamous (BS) cervical epithelium, progresses toward invasive cancer (far right). Precancer is commonly grouped into three stages (CIN 1-3). Cervical epithelium often remains precancerous for a long time (e.g. 15-20 years) before developing into invasive cancer. This leaves ample time for detection by an effective screening modality.

Figure 2:
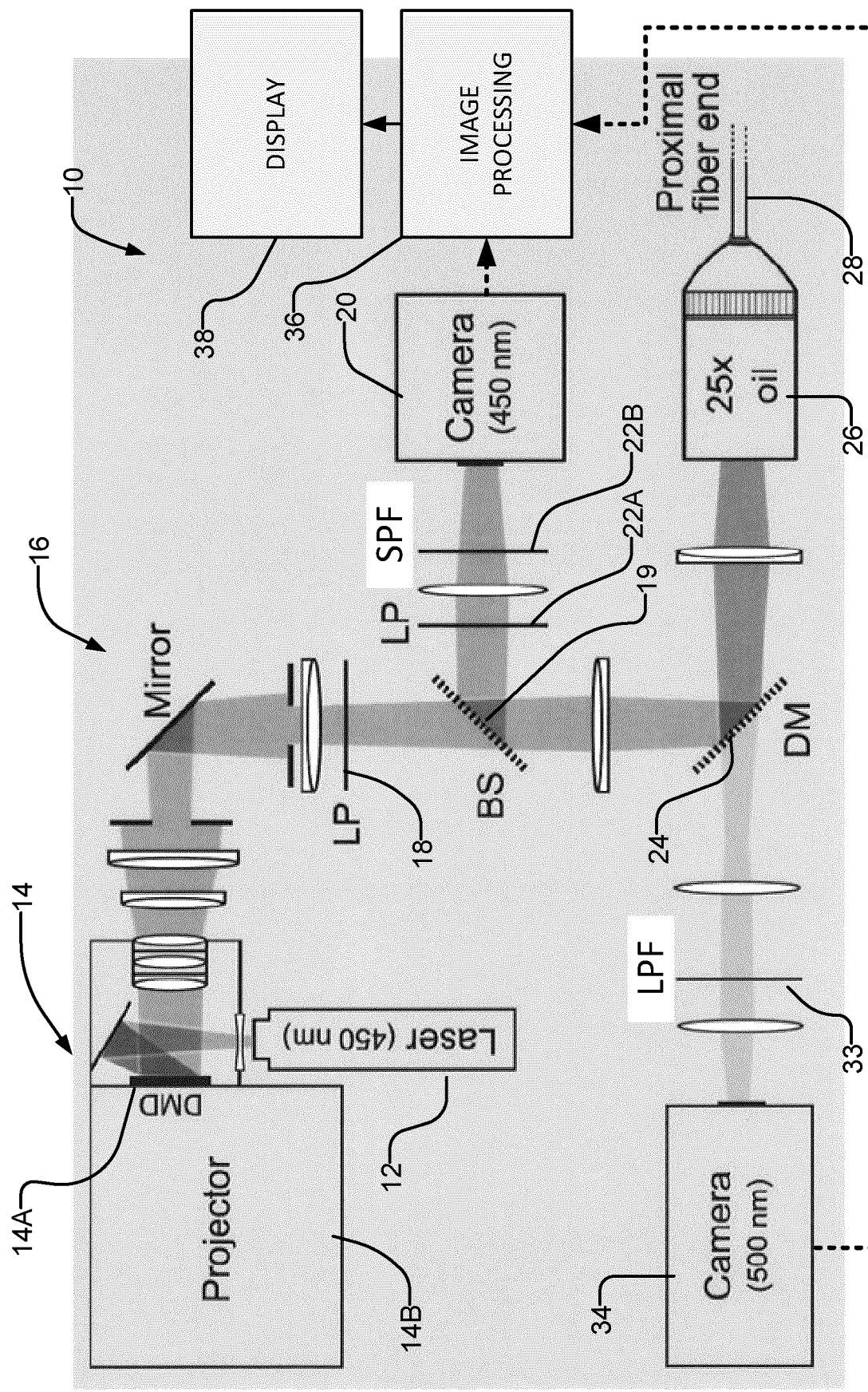
FIG. 2 is a schematic illustration of a system for combined fluorescence and diffuse optical microscopy imaging.

FIG. 2 schematically illustrates a system 10 which may be used for simultaneous diffuse optical microscopy (DOM) and fluorescence endomicroscopy (FE) imaging according to an example embodiment. System 10 comprises a light source 12 which is substantially monochromatic. Light source 12 may, for example, comprise a laser light source. The wavelength of light source 12 may be selected to facilitate imaging by both DOM and FE. For example, light source 12 may emit light in a wavelength range of 300 nm to 600 nm. In a preferred embodiment light source 12 emits light having a wavelength of approximately 450 nm (e.g. 450 nm±10 nm or 450 nm±5 nm or 445 nm±5 nm). The wavelength of light source 12 may be selected to correspond to a wavelength which excites fluorophores of a dye (for example acriflavine hydrochloride (AH)) used for FE.

Light source 12 has sufficient power to yield satisfactory images as described herein. For example, light source 12 may have a power output in the range of 30 mW to 100 mW. As a non-limiting example, light source 12 may have a power output of 70 mW.

Light output by light source 12 is spatially modulated by a light modulator sub system 14. Light modulator subsystem 14 spatially modulates the light from light source 12 at a desired spatial frequency. The spatial modulation may be applied in one or two dimensions.

In the illustrated embodiment, spatial light modulator subsystem 14 comprises a digital mirror device (DMD) 14A driven by projector circuitry 14B. To facilitate wide field projection, the beam from light source 12 may be widened and directed to DMD 14A by way of an optical diffuser plate and a lens.

The spatial modulation may be defined by image data supplied to projector circuitry 14B. The image data may, for example, comprise plural parallel stripes or an array of spots with a separation between the stripes or spots corresponding to the desired spatial frequency. For example, the spatial frequency may be in the range of 2 mm$^{-1}$ to 20 mm$^{-1}$.

In some embodiments the modulation is sinusoidal in one or two dimensions. For example, structured illumination patterns may be of the form:

$$I(x, y) = \hat{I}\left(\frac{1 + \sin(2\pi fx + \varphi)}{2}\right) \text{ or } I(x, y) = \hat{I}\left(\frac{1 + \sin(2\pi fy + \varphi)}{2}\right)$$

or a combination of both
where: I is intensity as a function of position (x,y); Î is a maximum amplitude of the structured light; f is the spatial frequency; and φ is a phase factor.

Light modulated by spatial light modulator subsystem 14 is projected onto a surface of a patient's tissue T (See FIG. 3) to be studied. In the illustrated embodiment the light is projected by an optical system 16 comprising an arrangement of lenses and mirrors that delivers the spatially modulated light to an objective lens 26. Objective lens 26 may, for example, comprise an oil immersion microscope objective providing demagnification of the structured light pattern by a suitable factor such as 25X. Optical system 16 demagnifies the structured illumination patterns to fit the aperture of objective lens 26.

Objective lens 26 couples the light into a fiber bundle 28 that carries the light to the end of a probe 30 arranged to illuminate tissue T with structured light and to collect light from tissue T. Fiber bundle 28 may have a length sufficient to reach the epithelial tissues to be imaged. For example, fiber bundle 28 may have a length of 1½ m or so.

In an example embodiment fiber bundle 28 comprises a coherent fiber bundle (FIGH-30-850N, Myriad Fiber Imaging) comprising 30,000 imaging fibers with a circular imaging field of view of 790 μm in diameter. The polished proximal end of fiber bundle 28 is placed at the working distance of objective lens 26. Index-matching immersion oil is placed between objective and fiber bundle to suppress reflections at the fiber interface.

Figure 3:
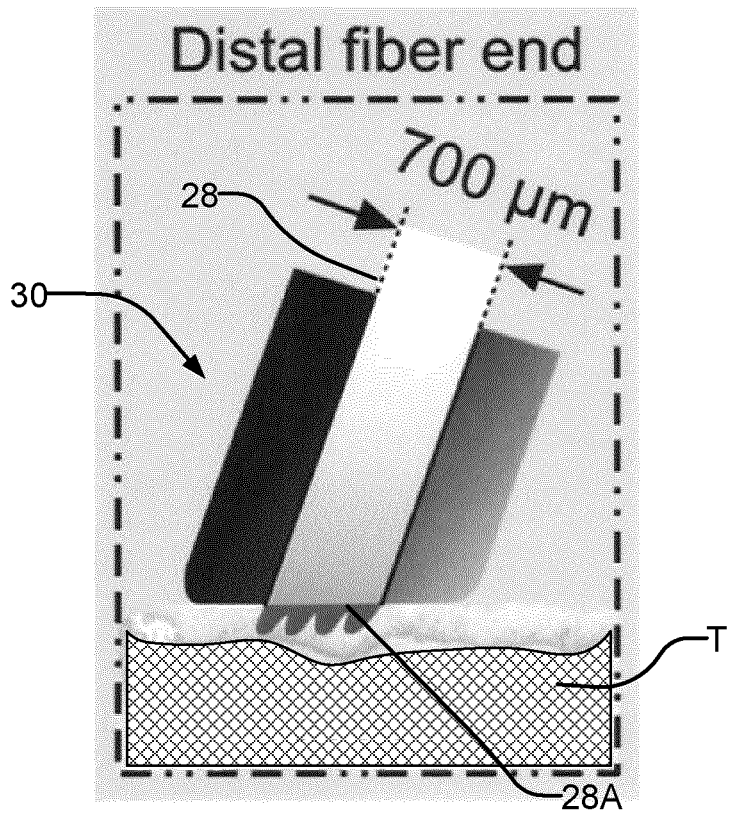
FIG. 3 is a schematic illustration showing a probe for the system of FIG. 2.

The distal end of fiber bundle 28 is located at a probe 30 which may be put in contact with the surface of tissue T (FIG. 3). To avoid reflections from the distal ends of the fibers of fiber bundle 28 the distal end of fiber bundle 28 may be polished at a suitable angle (such as 20 degrees). In a prototype embodiment the fiber projection and detection numerical aperture was 0.27±0.02.

In the illustrated embodiment the optical system includes a linear polarizer 18, a beamsplitter 19 and a dichroic mirror 24. The spatially modulated light is passed by beamsplitter 19 and dichroic mirror 24.

The light collected from tissue T may include backscattered light. The backscattered light may result at least in part from light scattering at loci corresponding to sub-cellular refractive index variations in tissue T. Some of the scattered light is diffusely reflected and captured by a camera 20. The scattered light has the same wavelength as the incident structured light.

In the illustrated embodiment backscattered light returns through fiber bundle 28 and objective lens 26 and is reflected by dichroic mirror 24 and beamsplitter 19 into an arm leading to camera 20. The light may pass through a linear polarizer 22A and a short pass filter 22B. Short pass filter 22B blocks any longer-wavelength fluorescence light from being captured by camera 20. Crossed polarizers 18 and 22A reduce contributions to the reflectance signal at camera 20 due to specular reflections in the optical setup.

The wavelength of light source 12 is selected to induce fluorescence at fluorophores of tissue T. Some of the fluorescence light is emitted in directions such that the fluorescence light is captured at probe 30 and delivered by fiber bundle 28 to dichroic 24 by way of objective lens 26. The fluorescence light has a longer wavelength than the incident structured light. Dichroic 24 is selected to pass the fluorescence light to camera 34. In the illustrated embodiment the light path to camera 34 includes a long pass filter 33. Long pass filter 33 blocks any residual reflected light from being captured by camera 34.

Images captured by cameras 20 and 34 may be delivered to an image processing system 36. Output images may be displayed on a display 38. Image processing system 36 may comprise a data processor such as one or more microprocessors and/or one or more graphics processors configured by software instructions to perform image postprocessing steps to reduce image artifacts and to enhance perceived image quality.

In an example embodiment images from cameras 20 and 34 are transmitted to image processing unit 36 by way of high speed interfaces. The images are optionally cropped to a region of interest and/or reduced in size. This reduces the amount of data to be processed and may speed up data processing. Size reduction may be performed, for example, by one or more of down sampling, hardware binning and software binning. In cases where the resolution is limited by the number of fibers in fiber bundle 28 this size reduction may significantly speed up image processing operations without removing valuable information.

In a prototype embodiment reflectance images captured by camera 20 were reduced to a size of 256×256 and fluorescence images captured by camera 34 were reduced to a size of 512×512 pixels. As the effective resolution of both cameras 20, 34 was much higher than that of the 30,000 fiber imaging bundle in the prototype embodiment, this size reduction enhanced computational speed and the lost resolution was not supported by the fiber bundle or imaging mode.

The images may be processed in various ways including:
  subtracting dark reference frames which may, for example, be obtained by immersing the tip of probe 30 in a dark water-filled container while running the structured illumination patterns. The dark reference permits internal reflections and fluorescence within system 10 to be quantified and subtracted.
  high-pass spatial filtering to compensate for differences in the integrated intensity for different phase shifts of the structured illumination. Such differences may arise as a result of the limited diameter of fiber bundle 28 and may result in ringing artifacts in the computed reflectance image (especially for low spatial frequencies).
  divide reflectance images by flat fields to compensate for differences in intensity, and focus and uniformity of the structured light patterns in different areas within the projected structured light patterns. The flat fields may, for example, be generated by obtaining reflection images of freshly prepared intralipid emulsions with a reduced scattering coefficient.
  compensate for fiber bending and tissue-probe interface variations which influence projection and collection efficiencies of individual fibers and give rise to superimposed image noise patterns. Such noise patterns are often very similar in adjacent imaging iterations. Compensation may comprise subtracting a time lapse average of preceding imaging iterations. In some embodiments such compensation is applied to displayed output images but not to images used for quantitative evaluation.

Image processing 36 may perform these and/or other image processing in real time.

It can be appreciated that apparatus 10 may be operated to simultaneously obtain both DOM and FE images of a patch of tissue T.

DOM Imaging

Figure 4:
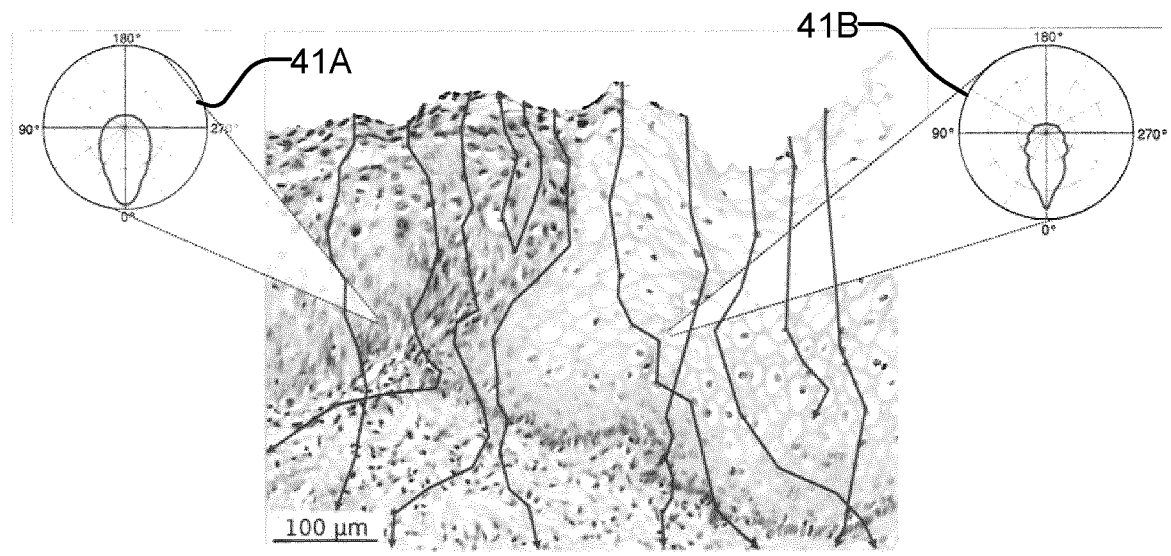
FIG. 4 is a view of a tissue cross section showing possible trajectories for photons as a result of scattering in the tissue.

FIG. 4 illustrates the source of backscattered light. Typical paths for light propagating through epithelial tissue are indicated by lines. The light is scattered at loci where there is a variation in the index of refraction. The likelihood that a photon will be scattered in a particular direction can vary from place to place as indicated by plots 41A and 41B. Every scattering interaction reflects the tissue micro- and nano-structure in a complicated way. The sum total of these scattering interactions causes some of the incident light to be backscattered into probe 30 and carried to camera 20 by way of fiber bundle 28. Changes to the tissue micro- and nano-structure resulting from precancer or cancer can cause changes in the backscattered light that can be observed in the images acquired by camera 20.

Figure 5:
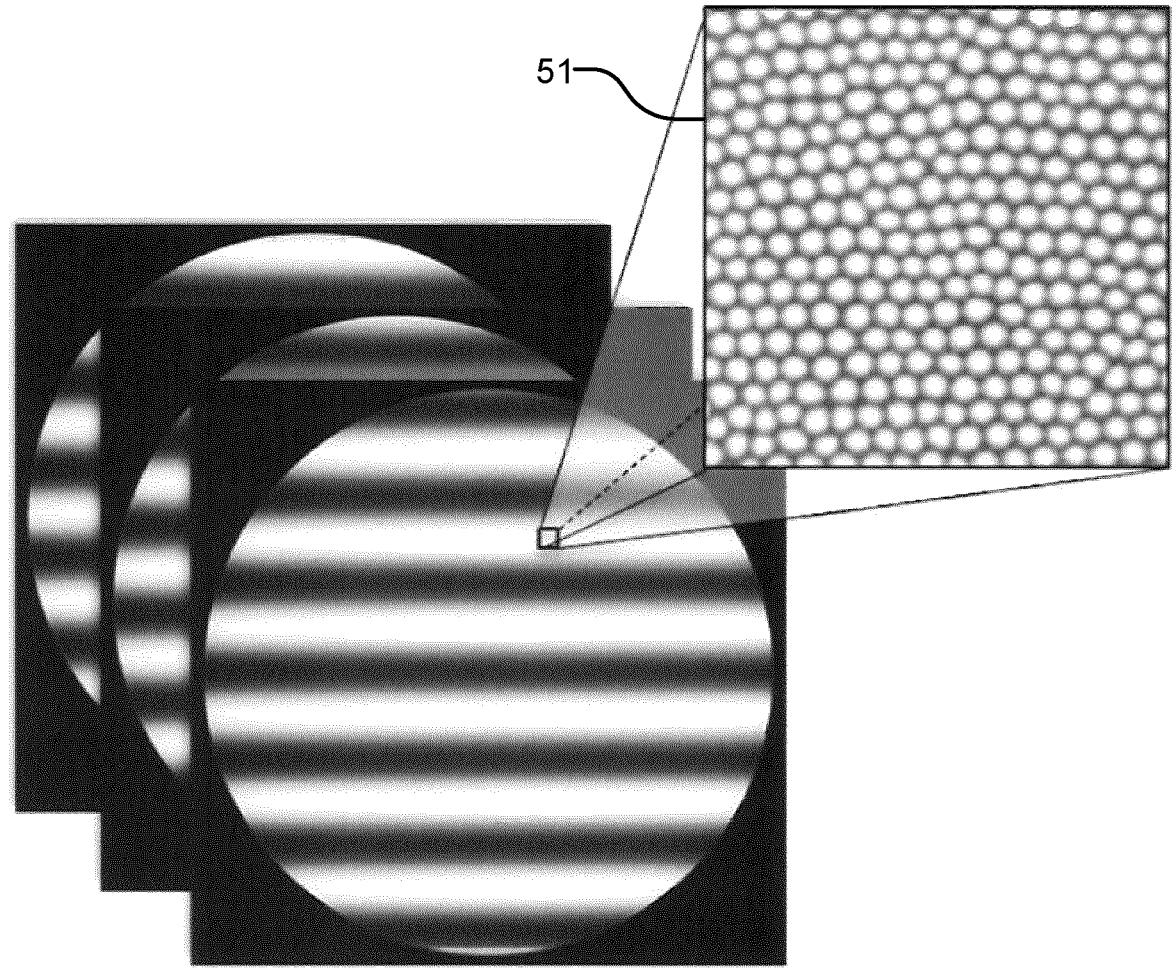
FIG. 5 shows a set of structured illumination patterns and a backscattered image.
Figure 6A:
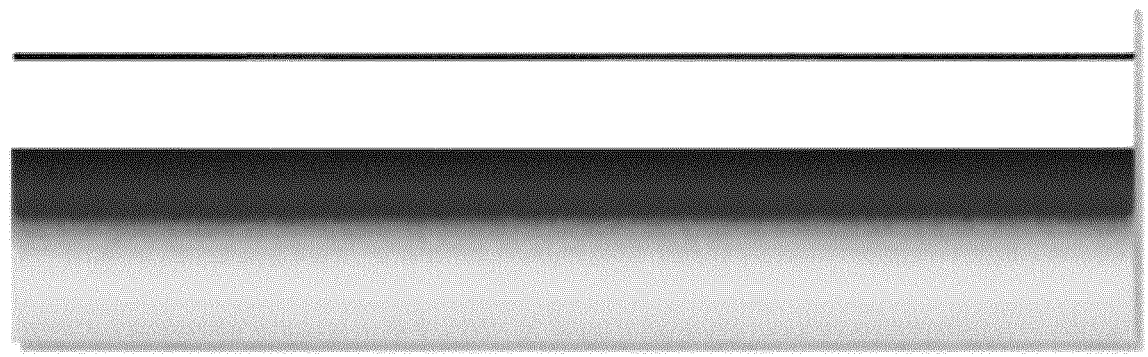
FIGS. 6A to 6D illustrate the effect of structured illumination fields having different spatial frequencies on the penetration into tissue of light from the structured illumination.
Figure 6B:
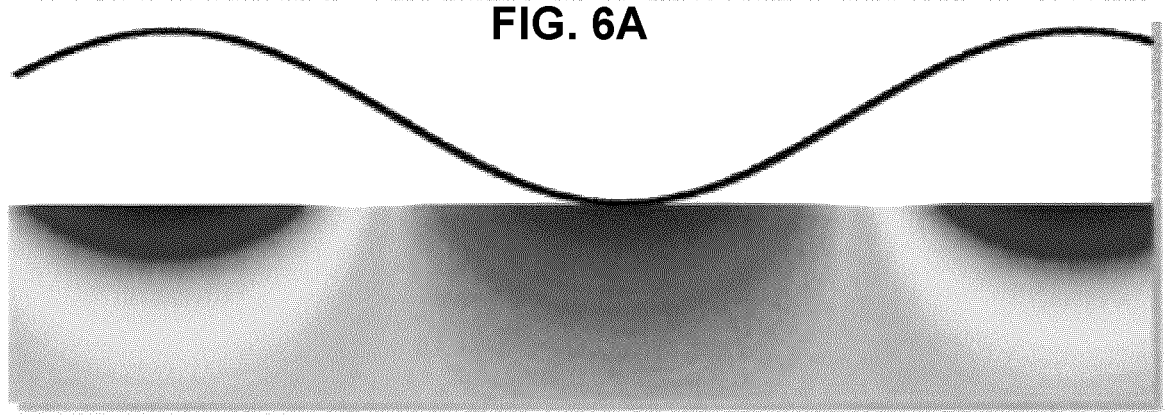
Figure 6C:
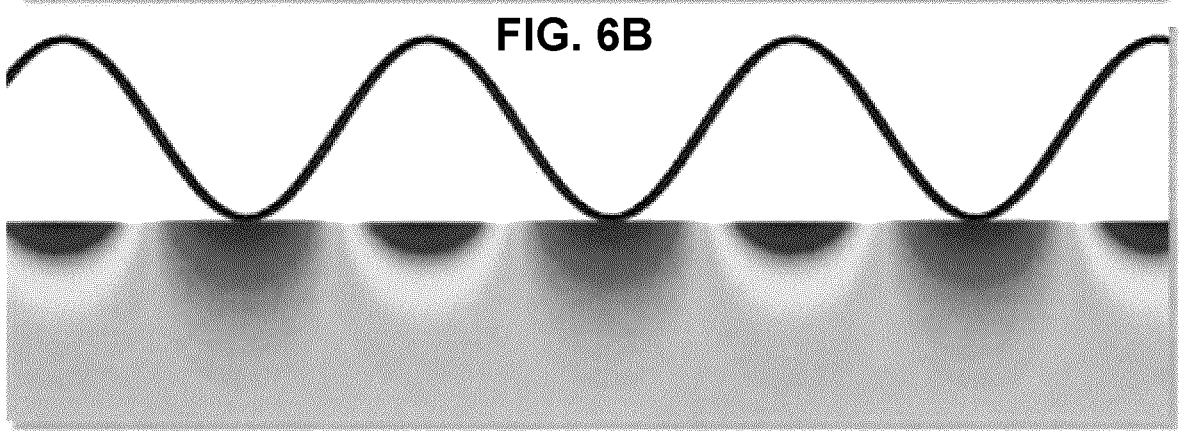
Figure 6D:
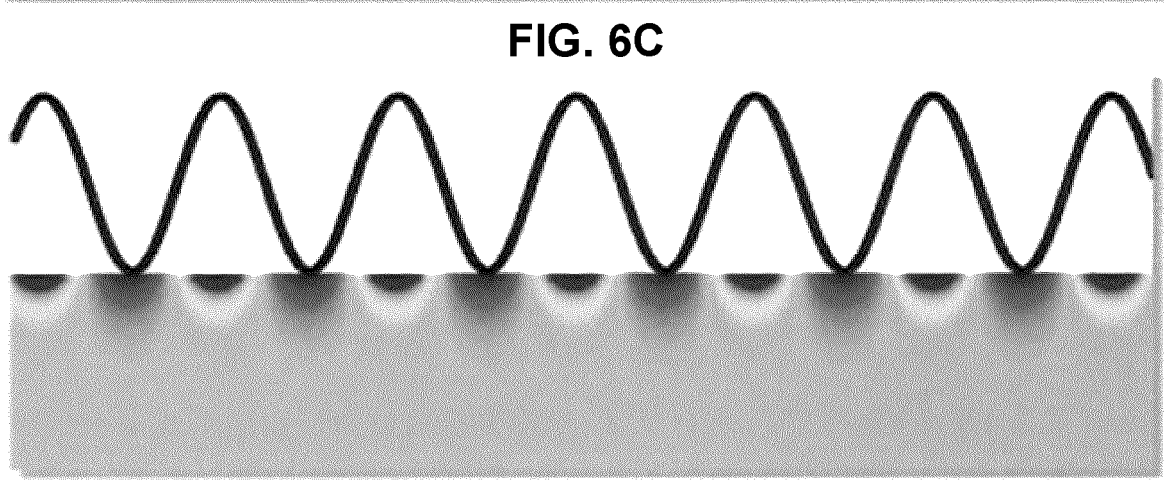

FIG. 5 shows patterns of structured light on a surface of tissue T and a resulting portion of an image 51 as may be acquired by camera 20. Changing the spatial frequency of the structured illumination pattern allows adjustment of the degree of surface sensitivity. For reflectance mode (DOM) imaging one may select a spatial frequency of the structured light to tailor sensitivity towards backscattering from different epithelial depths. The spatial frequency of the structured light may be altered, for example, by changing the setting of DMD 14A.

FIGS. 6A to 6D illustrate the effect of spatially modulating the light incident on tissue T at different spatial frequencies (which may be described by line pair/mm or lp/mm). As the spatial frequency at which the light is modulated is increased, backscattered light that is returned through fiber bundle 28 tends to originate from shallower depths in tissue T.

Figure 7:
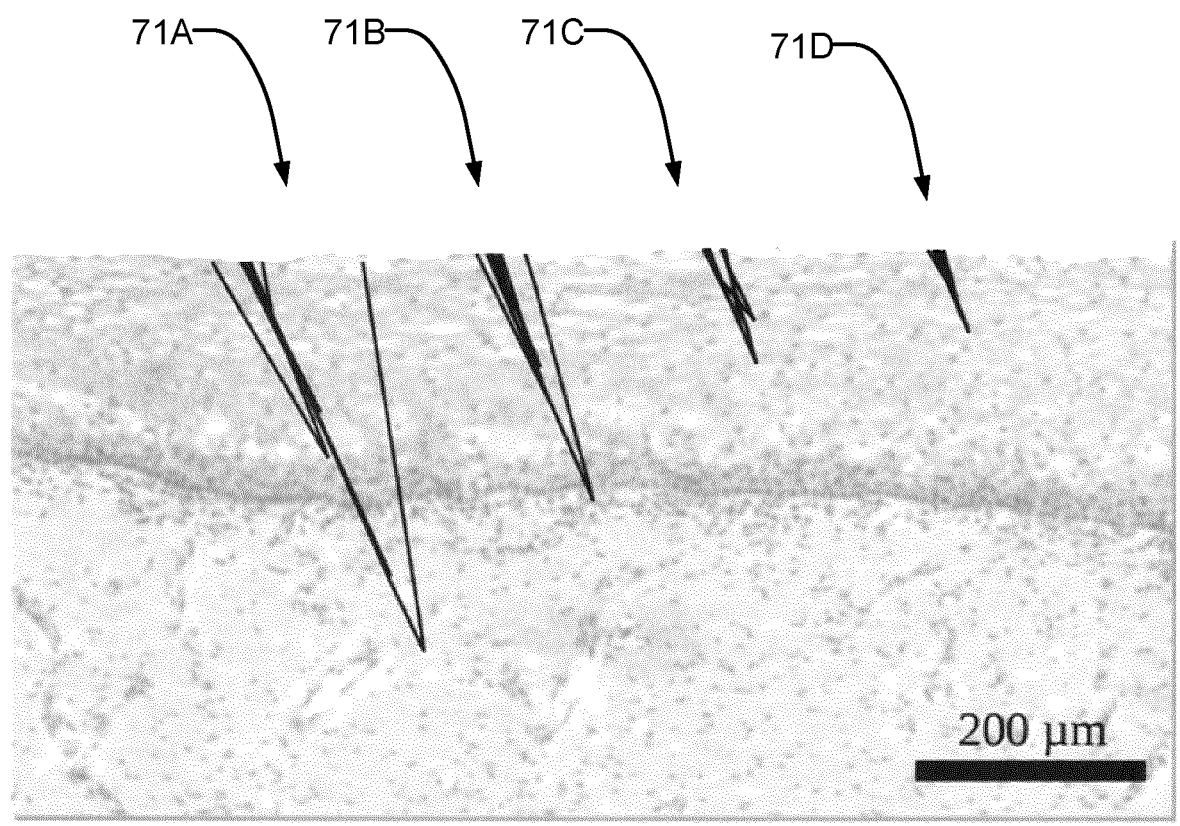
FIG. 7 is a cross section through an epithelial tissue with overlaid lines representing modeled penetration of photons into the tissue from structured illumination of different spatial frequencies.

FIG. 7 shows simulated light paths for different structured illumination patterns having spatial frequencies of: f=3 lp·mm$^{-1}$ (71A); f=6 lp·mm$^{-1}$ (71B); f=9 lp·mm$^{-1}$ (71C); and f=15 lp/mm$^{-1}$ (71D).

In some embodiments the phase of the structured illumination pattern may be changed. Such a phase shift may be obtained by shifting the structured illumination pattern by a fraction of a wavelength of the structured illumination pattern in a direction in which the intensity of light in the structured illumination varies (e.g. where the structured illumination pattern comprises stripes the shifts may be in a direction perpendicular to the stripes). Camera 20 may be operated to obtain an image for each phase. The resulting images may then be used to compute a single image.

The phase shifts may be equal. For example n phase shifted images may be acquired with the structured illumination pattern shifted by phases of 0, $2\pi/n$, $4\pi/n$, . . . , $(2n-2)\pi/n$ where a shift of $2\pi$ equals one wavelength.

In a prototype embodiment three successive captures corresponding to phase shifted structured illumination patterns (see FIG. 5) are used to compute a single image with enhanced surface contrast. In this example, the structured illumination pattern may be phase shifted by 0, $2\pi/3$ (120 degrees) and $4\pi/3$ (240 degrees), respectively, for the three phase images.

With the three reflectance phase images captured by camera 20 denoted by $X_1$; $X_2$; $X_3$. Combined reflectance values R for a given spatial frequency and pixel location may be given by:

$$R = \frac{\sqrt{2}}{3}\sqrt{(X_1-X_2)^2 + (X_2-X_3)^2 + (X_3-X_1)^2}$$

Another example way to combine two or more images is to average the pixel values for the plurality of images. This yields an estimate of the case where the spatial frequency f=0 (uniform illumination).

Figure 8A:
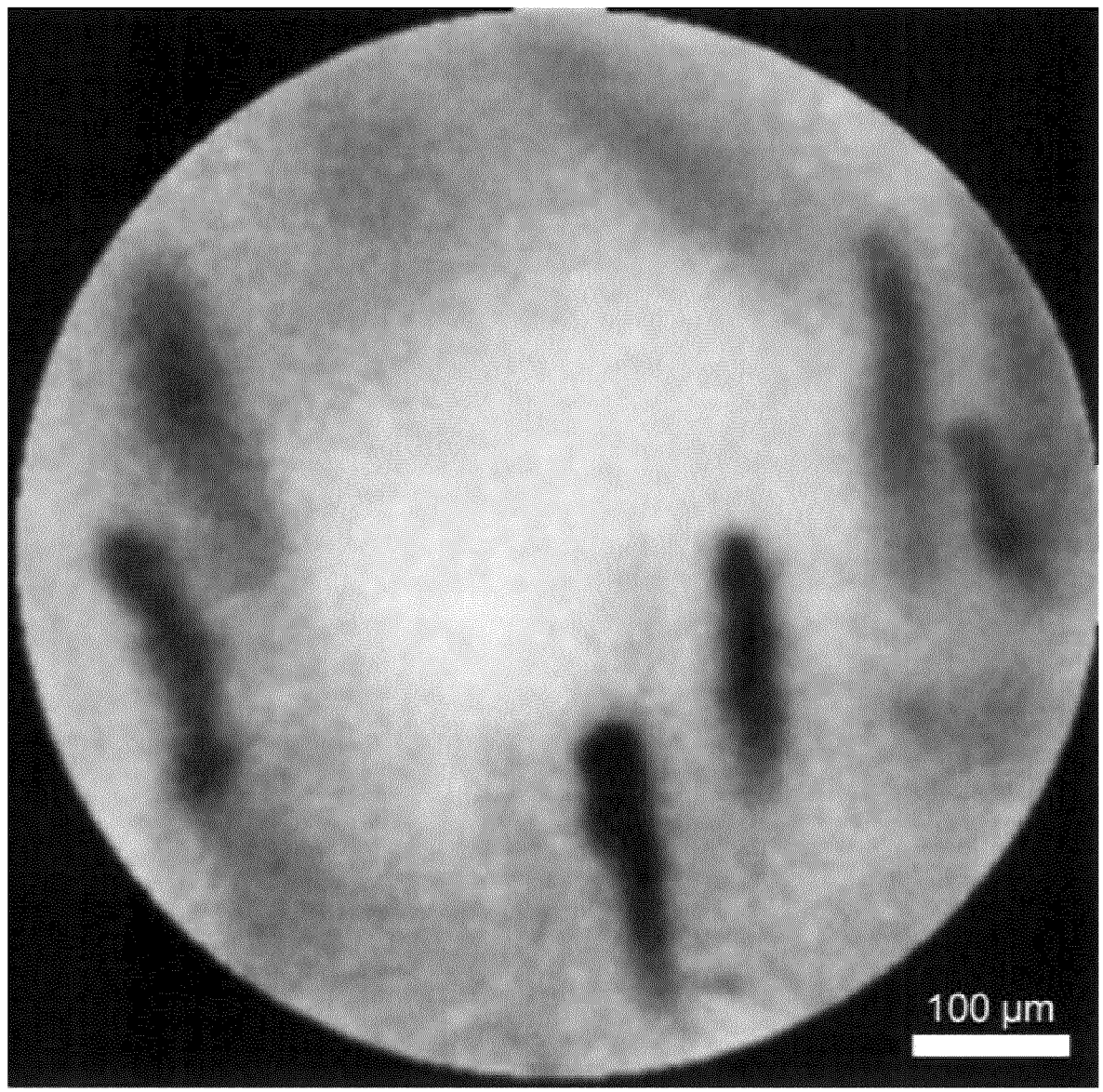
FIGS. 8A to 8E are example diffuse optical microscopy reflectance images.
Figure 8C:
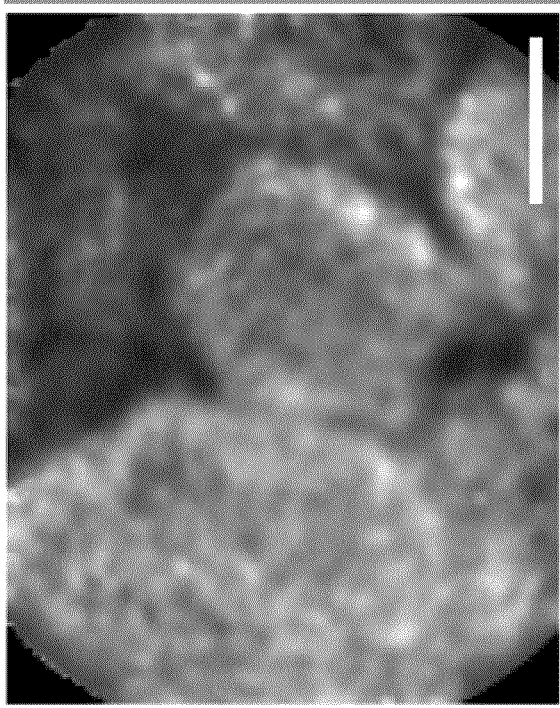
Figure 8B:
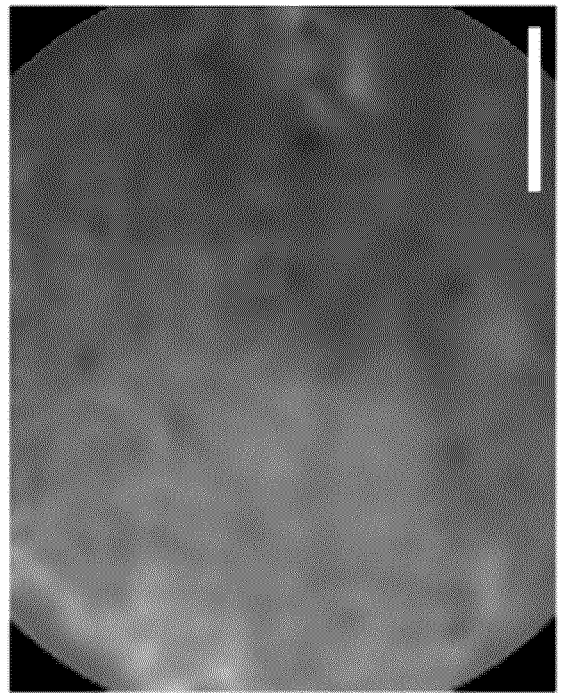
Figure 8E:
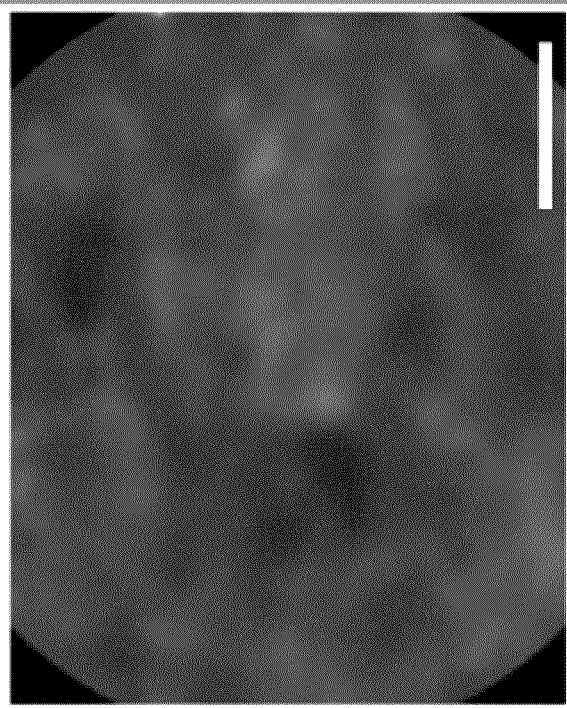
Figure 8D:
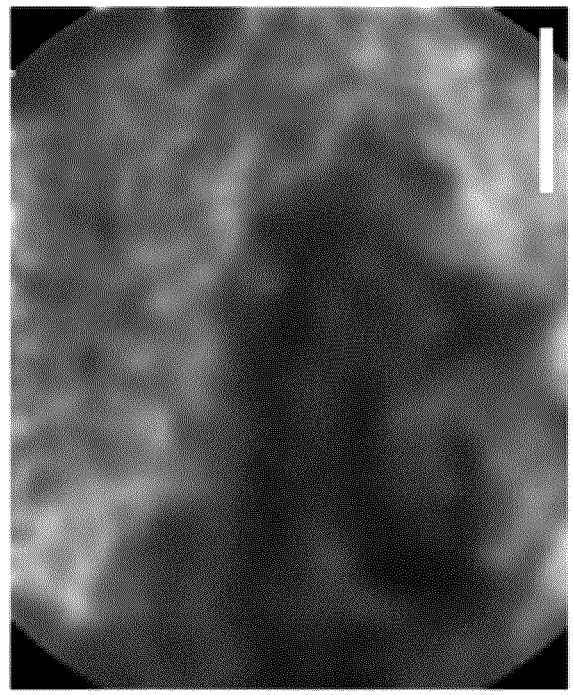

FIG. 8A is an example reflectance image captured from epithelium in the oral cavity. The reflectance image quantifies backscattering and displays light-absorbing blood vessels. FIGS. 8B through 8E are reflectance images quantifying backscattering from cervical epithelium in diffuse optical microscopy. Different epithelial locations reveal different intensity and heterogeneity in backscattering. Bright areas correspond to regions of enhanced backscattering which may originate in nuclear enlargement and crowding.

Measures Based on Different Spatial Frequencies of Structured Illumination

Figure 9:
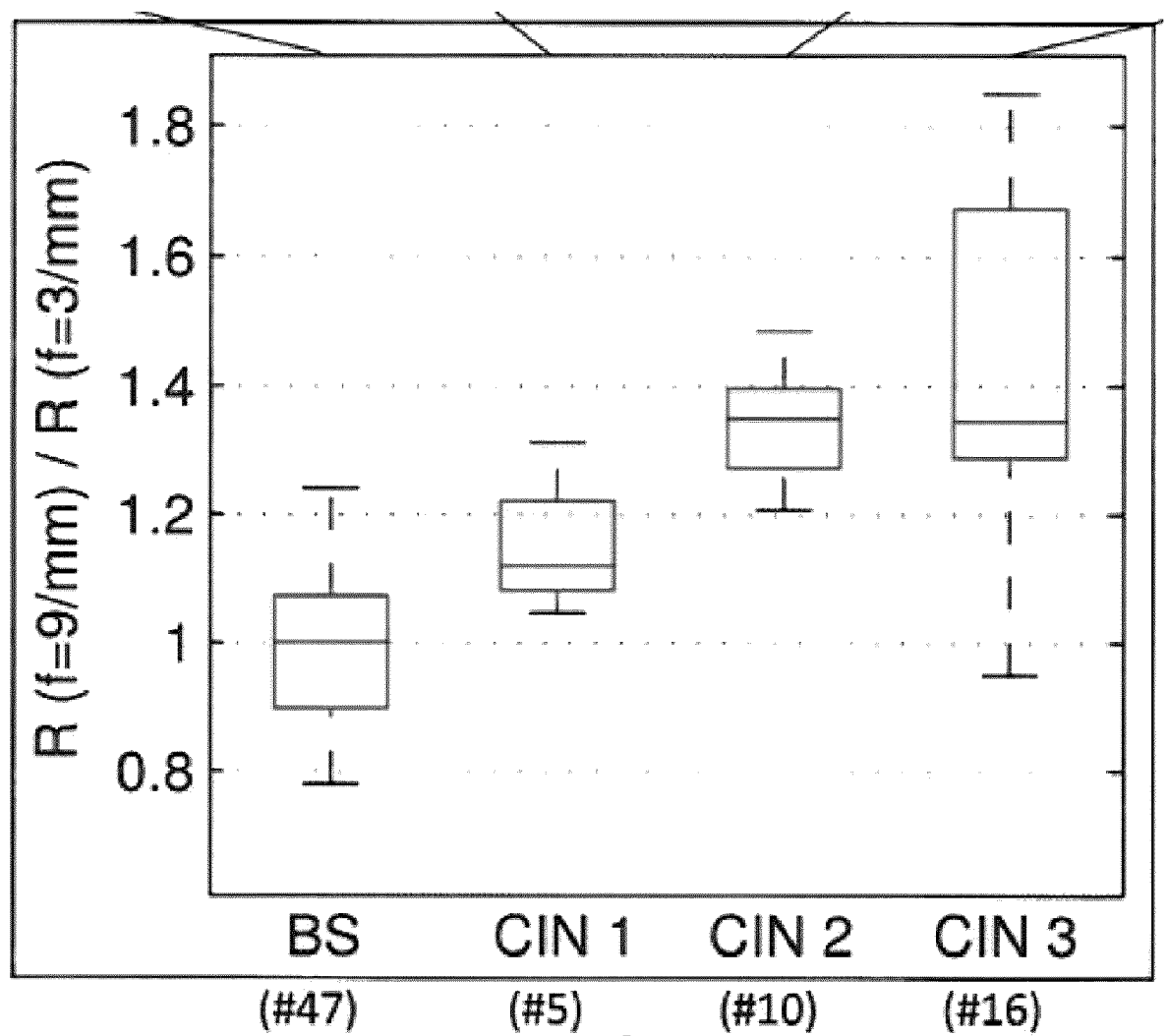
FIG. 9 is a box chart illustrating a correlation between a ratio of reflectance for different spatial frequencies of structured illumination and dysplasia.

There is a correlation between the stage of precancer or cancer and the way that tissue images differ with the spatial frequency of the structured illumination. For example, studies on cervical squamous epithelium have revealed a correlation between depth dependent epithelial backscattering and the different stages of precancer. FIG. 9 shows this correlation in a box plot which quantifies the ratio of absolute backscattering for two different spatial projection frequencies (9/mm and 3/mm). FIGS. 9A through 9D, respectively, show sections through the tissues corresponding to the BS, CIN 1, CIN 2 and CIN 3 bars of FIG. 9. The scale of FIGS. 9A to 9D is 400 μm from the top to bottom of each image.

Since different spatial frequencies of structured illumination interrogate different depths in the epithelial tissue, FIG. 9 shows correlations between grade of epithelial dysplasia and relative depth-dependent shifts in light backscattering.

In some embodiments of the present invention a controller controls light modulator subsystem 14 to switch between two (or more) spatial frequencies of the structured illumination. For each spatial frequency light modulator system may be controlled to generate the structured illumination with different phase shifts as described above. Camera 20 may be operated to capture the resulting images, the system may process the resulting images to combine the phase shifted images for each spatial frequency into a combined image and to compute ratios (R) of the pixel values in the combined images for the different spatial frequencies.

To compensate for differences between patients and between locations the R values may be normalized by the corresponding mean ensemble value obtained from reflectance images taken at an adjacent or contralateral normal reference for the patient.

Images may be obtained using structured illumination of different spatial frequencies at closely spaced times such that the images remain co-registered. Since spatial light modulation subsystem 14 may be able to switch illumination patterns very rapidly it is possible to interleave sets of images of different spatial frequencies. For example, with two spatial frequencies (SF1, SF2) of structured illumination and three phase shifts (PS1, PS2, PS3) for each spatial frequency one could obtain images using camera 20 in the sequence SF1+PS1, SF2+PS1, SF1+PS2, SF2+PS2, SF1+PS3, SF2+PS3 or any other order.

In some embodiments system 10 is configured to compare the different phase images to detect motion artifacts (which result in differences in the area of tissue viewed by the different phase images) and to automatically discard sets of images which include motion artifacts.

A ratio image in which displayed pixel values are based on the ratios R may be displayed on a display of system 10. For example, different ratios may be presented as different colours, different intensity of highlighting, or the like.

Statistics for the ratios may be calculated for regions within the ratio image. For example a mean, median or other representative value of the ratio may be computed for a central area of a ratio image. Such statistics may optionally be used to control an indicator. For example, when a representative value of the ratios for pixels in a defined area of the ratio image crosses a threshold a light, audible indicator or the like may be triggered. System 10 may generate and display an indication of an estimated degree of dysplasia corresponding to the representative value of the ratio.

As another example, DOM images for different spatial frequencies of structured illumination may be compared (for example by computing a measure of correlation). DOM reflectance images at different spatial frequencies for more highly dysplastic epithelium tend to appear more heterogeneous as compared to corresponding images in a normal epithelium. Such heterogeneity can result in a reduced correlation between the images acquired for different spatial frequencies. In some embodiments a signal is given where a computed measure of correlation between DOM reflectance images for different spatial frequencies of structured illumination indicates a low correlation (e.g. the correlation measure has crossed a predetermined threshold.

Fluorescence Imaging

The light from light source 12 partly excites extrinsic fluorophores in the top layers of tissue T to emit fluorescence. A nuclei staining extrinsic fluorophore dye may be applied to make the fluorescence signal indicative of nuclear density. The fluorescence has a longer wavelength than the light from light source 12 (e.g. light source 12 may emit blue light having a wavelength of about 450 nm while the fluorescence may be green light having a wavelength of about 500 nm). Dichroic mirror 24 separates green fluorescence light from the blue backscattered light. Fluorescence images are obtained by camera 34.

Figure 8F:
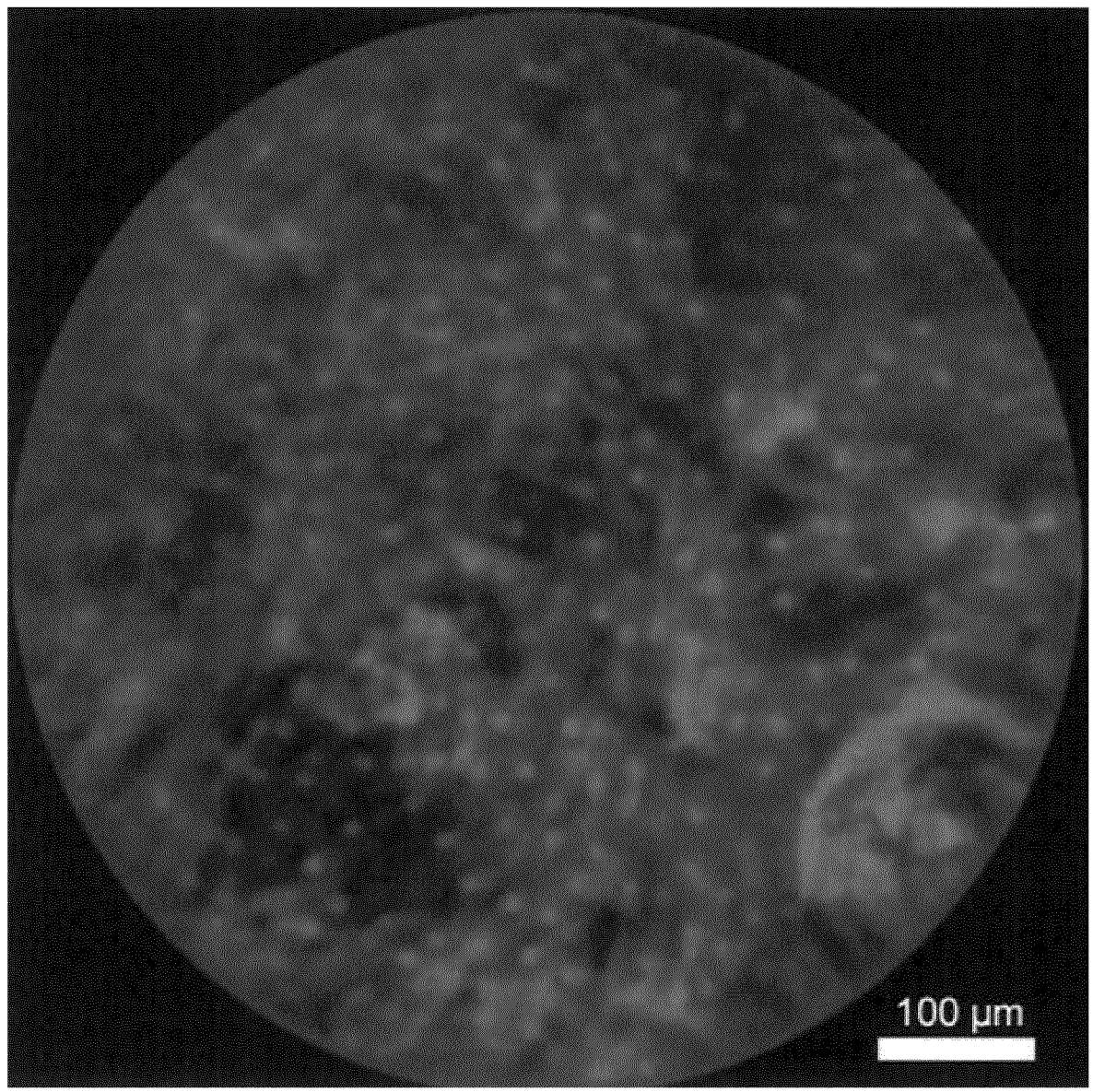
FIG. 8F is a fluorescence endomicroscopy image acquired simultaneously with the diffuse optical microscopy reflectance image of FIG. 8A.

The FE images can be obtained using the same spatially modulated illumination as the DOM images. The structured illumination allows for optimizing contrast towards the uppermost cell layers. Plural fluorescent images corresponding to different phase shifts of the spatial modulation of the structured illumination may be obtained and combined in the same manner described above for DOM images. FIG. 8F shows an example FE image acquired simultaneously with the reflectance image of FIG. 8A. The FE image reveals the distribution of cell nuclei.

Because FE images can be obtained simultaneously with DOM images, coregistration between the FE and DOM images can be guaranteed. FE images and DOM images may by simultaneously recorded at a rate of, for example, 16 frames per second.

FE and DOM images may be displayed on a display for review by a physician or other person using system 10 to perform tissue screening or assessment. These imaging modalities provide complementary information. In some embodiments DOM and FE images are displayed simultaneously next to one another so that they can be easily reviewed together and compared. When combined, DOM and FE modalities provide diagnostic sensitivity to both moderate and severe epithelial dysplasia in vivo. FE using a nuclei staining extrinsic fluorophore dye can image the nuclear structure of the most superficial epithelial cell layers. The dye contrast helps to reveal severe dysplasia which affects nuclear size and density in the surface layers of the epithelium. However, FE on its own is mostly unable to detect moderate dysplasia where structural alterations are limited to deeper cell layers. As described above, DOM using appropriate selection of structured illumination patterns allows light penetration to be tailored to diagnostically meaningful depths within the epithelium. This provides added sensitivity toward moderate dysplasia.

System 10 may automatically process FE images to obtain various measures such as measures of the nuclear-to-cytoplasmic ratio that are relevant to tissue characterization.

Combined FE/DOM Images

Since the DOM and FE images are co-registered it is also simple to create a composite image based on simultaneously-acquired DOM and FE images. Pixel values from the DOM and FE images may respectively be applied to control different attributes of the composite image.

For example, pixel values from the DOM and FE images may respectively be applied to control different colors in the composite image or pixel values from one of the images may be applied to control brightness of the image and pixel values from the other one of the images may be applied to control color of pixels in the composite image. As another example, the composite image may be generated by using pixel values in one of the images to control highlighting superposed on the other image. As another example pixel values in a composite image may be controlled in part by ratio values R for a ratio image as described above.

Combined FE/DOM Quantitative Analysis

Figure 10:
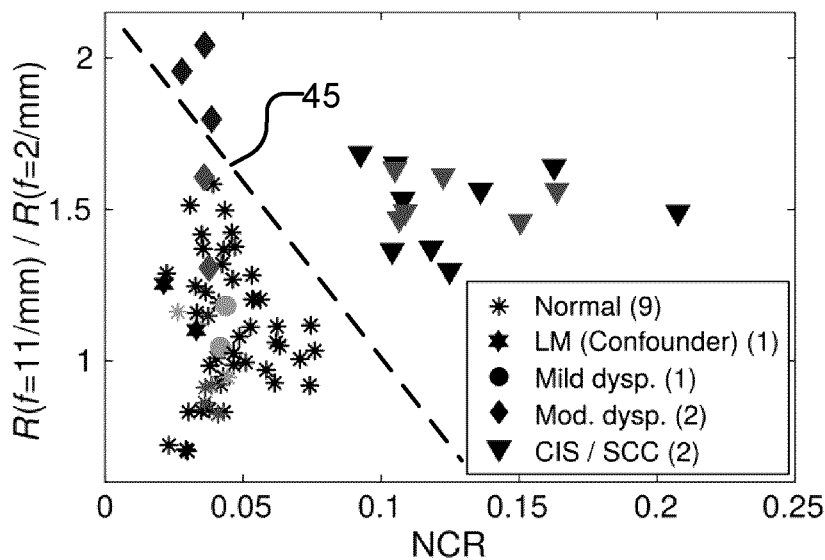
FIG. 10 is a scatter plot of nuclear-to-cytoplasmic ratio and ratios of reflectance for different spatial frequencies of structured illumination for a range of samples.
Figure 9A:
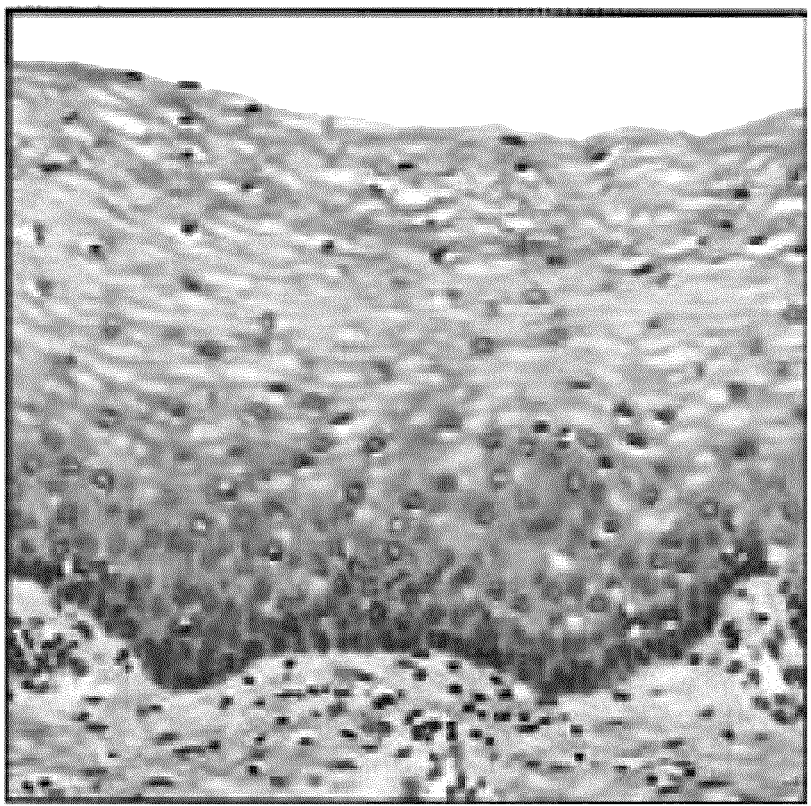
FIGS. 9A to 9D are cross sections of tissues respectively classified as BS, CIN 1, CIN 2, and CIN 3.
Figure 9B:
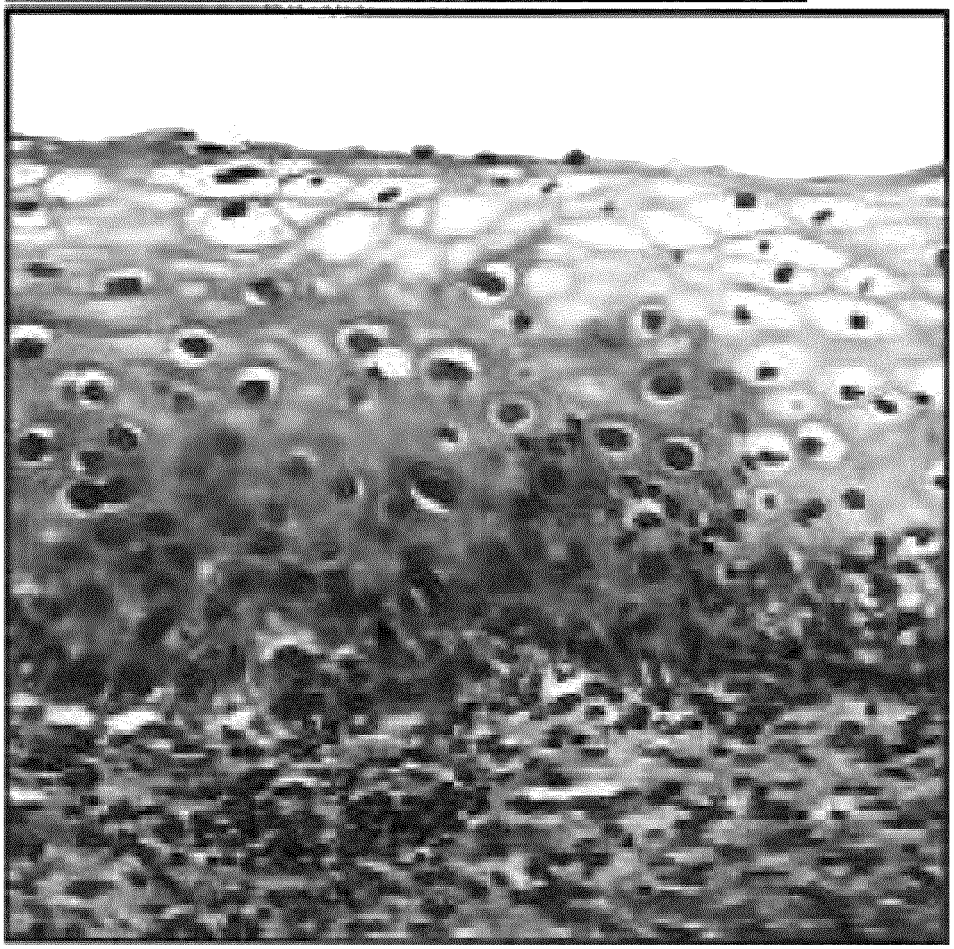
Figure 9C:
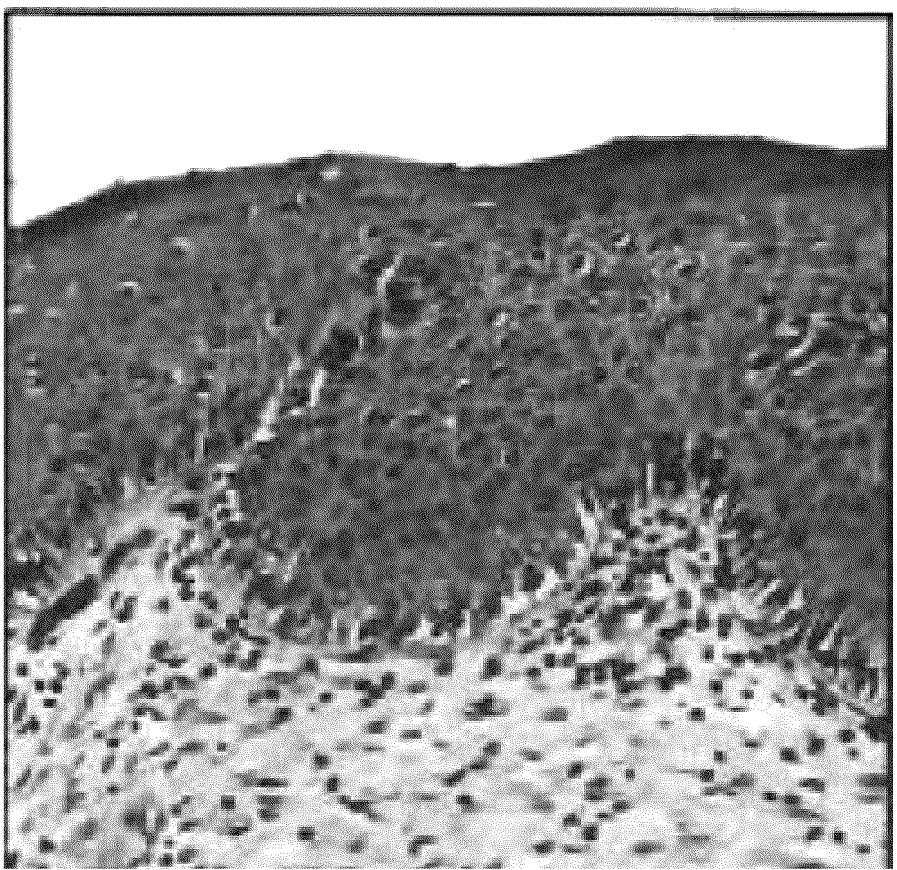
Figure 9D:
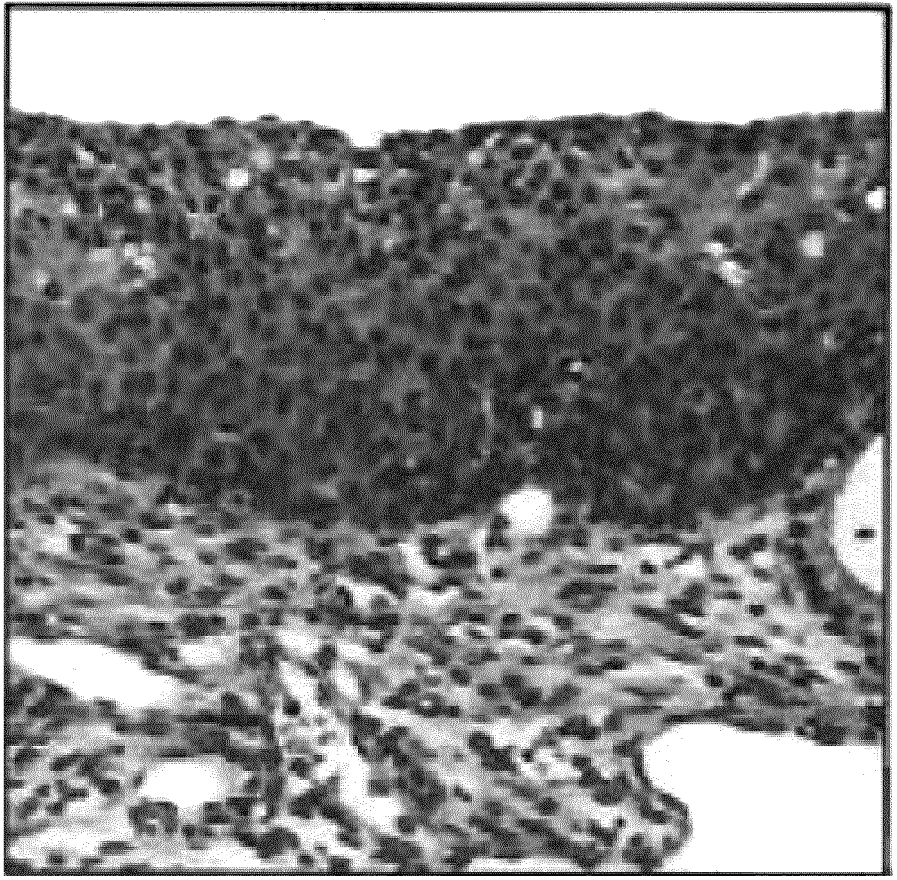

A FE image may be quantitatively analyzed to yield a measure of nuclear-to-cytoplasmic ratio (NCR, i.e., the perceived nuclear area density) in FE. Such a measure may be combined with a measure derived from DOM (e.g. a representative value for a ratio between different spatial frequency images) and the combination may be used to discriminate between normal tissues and tissues demonstrating various levels of dysplasia. FIG. 10 is a scatter plot with NCR determined from FE images on the horizontal axis and the backscattering ratio using DOM on the vertical axis. Every data point corresponds to an independent frame captured at a different tissue site of either the ventral or lateral tongue or the floor of mouth. The legend numbers state how many patients contribute to each data group. Data points for normal epithelium (asterisks) comprise imaging on both patients and on a healthy volunteer (30 years).

In some embodiments a discriminant analysis (e.g. a linear discriminant analysis) is performed by system 10. System 10 may be configured to generate a signal if the discriminant analysis detects a point on the side of a line (line 45 is provided as an illustration) dividing normal from abnormal results. System 10 may generate an output signal depending on which side of line 45 a computed point for a tissue being imaged is on or whether the point is close to being on the line. The output signal may be as simple as a green read or yellow light, a variable-length bar, a meter, or the like.

Example Usage

System 10 may, for example, be used to screen epithelial tissue of a patient by topically staining lesions of interest and one or more "normal" reference sites with a nuclei staining fluorescent dye such as AH. After staining, probe 30 may be placed on each lesion of interest and each reference site and held in place while reflectance and fluorescence images are simultaneously obtained as described above. Probe 30 may, for example, be held in place for approximately 1 second at each site. Resulting images may be displayed and stored as digital images for archiving and/or future review.

In some embodiments system 10 may be configured to analyze FE or DOM or both to sense high-grade dysplasia and trigger biopsy collection to confirm diagnosis. Analysis of DOM results may be applied to provide computed backscattering ratio images or average of image ratio values in real time as a measure for tissue abnormality. System 10 may provide various signals to inform a user of device 10 regarding characterization of the tissue being viewed by system 10 in real time.

There are multiple ways in which backscatter ratio images (ratios of backscatter for different spatial illumination patterns, lp/mm) may be presented to the user. These include:

- As simple numbers that represent the average image ratio values over an area of the image (e.g. the circular central ⅔rds or central ½ of the image. The areas may be chosen to be circular and not the entire image so as to avoid the boundary effects from the edge of the fiber bundle which can artificially distort the backscatter images and hence the ratios.
- As several separate images, one for each ratio of interest, to assist in the informed decision making process of the user, or
- As pseudo-colour images in which selected backscatter images of different illumination spatial frequencies are placed in the red, green and blue channels of a calculated image so that changes in these backscatter images will be observed as colour changes within the calculated image. This could assist in the informed decision making process of the user.
- As pseudo-colour images in which colour and/or intensity are set based on one or more ratios of reflectance in backscatter images for different spatial frequencies. In some embodiments the ratios are ratios for specific ranges of light wavelength (which may correspond to spectral bands of a multispectral camera as described herein).

Multi-Spectral Imaging

A system as described above may be modified to provide the option of multi-spectral imaging. In essence this may be done by replacing camera 20 with a multi-spectral camera 20A and adding an illumination source or sources 12A that provide an expanded set of illumination wavelengths.

Figure 11:
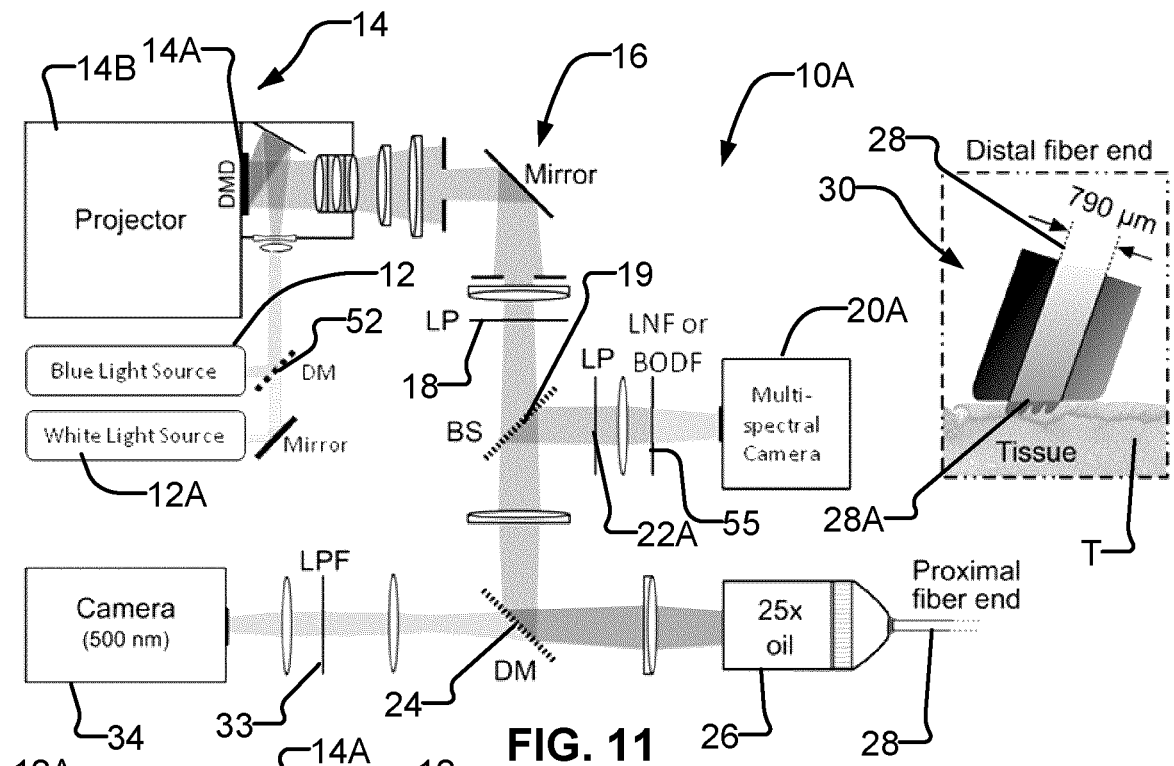
FIG. 11 is a schematic illustration of a system operable to provide combined fluorescence endomicroscopy and multi-spectral diffuse optical microscopy.

FIG. 11 shows an example system 10A which is similar to system 10 except that camera 20 has been replaced by a multi-spectral imaging camera 20A and an additional light source 12A is provided. In system 10A light from light source 12 is directed into optical path 16 by a dichroic mirror 52. Light from white light source 12A can pass through dichroic mirror 52. A filter 55 which may, for example, comprise a laser notch filter (LNF) or a blue optical density filter (BODF) may be provided in the arm of optical path 16 leading to camera 20A to block light from laser light source 12.

System 10A may operate in substantially the same manner as system 10 above to acquire DOM images except that the images acquired by camera 20A may be color images. Camera 20A may, for example, provide different bandpass filters for individual pixels in 2 by 2, 3 by 3 or 4 by 4 sub areas. In some embodiments, camera 20A is sensitive to light in more than five separate spectral bands. For example, camera 20A may have in the range of 9 to 16 distinct types of bandpass filters each type corresponding to a spectral band.

Light source 12A may, for example, comprise a white or soft white LED or a set of LEDs which emit light at different wavelengths.

In some embodiments light sources 12 and 12A are operated simultaneously. In such embodiments filter 55 may block or balance the light from light source 12 at camera 20A. In such embodiments light source 12 may comprise an intense blue LED. Filter 55 may comprise a blue optical density filter (i.e. a filter that transmits light having longer wavelengths than blue light with maximal transmittance but only partially transmits blue light) to reduce the blue backscattered light such that it does not saturate the multi spectral camera.

In other embodiments light sources 12 and 12A may be controlled so that only one of them is on at a time. System 10A may control camera 34 to acquire FE images while light source 12 is on and camera 20A to acquire DOM images while light source 12A is on.

Since different pixels in a typical multispectral camera are devoted to different spectral bands, multispectral cameras suffer a loss of resolution relative to monochrome cameras. However, in many cases the resolution of system 10A is limited by fiber bundle 28 such that the spatial resolution of multi-spectral camera 20A is not a limiting factor.

The additional information provided by multispectral DOM may be applied to improve disease differentiation through a variety of ways. These include:

Oxygenated and non-oxygenated blood have distinct absorption spectra and may therefore be distinguished in multispectral DOM images. This may help to distinguish blood vessels that have been recruited into metabolically active dysplasia from other blood vessels. The use of the spectral characteristics of blood along with the backscatter depth information from the structured illumination used for DOM may be applied to enable a refined depth of backscatter information selection including an estimation of the oxygenation state of the blood supply as a function of depth into the tissue.

Tissue backscatter is a function of wavelength, with shorter wavelengths of light travelling a shorter distance in tissue than longer wavelengths of light. The addition of spectral information enables one to combine the depth discrimination of spectral information with the depth discrimination of DOM for more precise backscatter depth determination. Since the depth within the epithelium of cellular differentiation disregulation determines to great extent the perceived grade of the dysplastic tissue, improved depth determination may provide improved disease detection and classification. This can be particularly important in tissue sites where the thickness of the epithelium can vary greatly such as the oral cavity.

Tissue Depth Measurement and Adjustment

Epithelial tissues can differ significantly in thickness (generally measured from the surface to the basement membrane). For example, the thickness of the epithelium is up to ~500 μm for the tongue but only ~150 μm for the cheek. Dysplasia is generally categorized based on the reach of deregulated differentiation relative to the thickness of the epithelium. For example, a tissue may be characterized by moderate dysplasia where deregulated differentiation reaches ½ to ⅔ the thickness of the epithelium (e.g. about 250 μm from the tissue surface in the tongue and about 75 μm from the surface in the cheek).

In some embodiments a system like system 10 or 10A is configured to estimate a thickness of the epithelium at the location of probe 30. This may be done in various ways. These include:

Analysis of DOM data. For example, using multispectral DOM the depth of the epithelium may be estimated by contrasting reflectance at larger wavelengths of the structured light pattern (e.g. 2 lp·mm$^{-1}$ vs. 5 lp·mm$^{-1}$ or uniform illumination vs. 5 mm$^{-1}$) and/or by contrasting reflectance at different wavelengths of light (e.g. green vs. red or near infrared (NIR)). Some embodiments may provide a separate light source (e.g. an IR or NIR light source) to provide longer wavelength optical radiation for use in depth measurements.

System 10 or 10A may include a separate depth measurement system that obtains a measurement of epithelial thickness. For example, probe 30 may include an ultrasound transducer that is operated to measure epithelial thickness.

System 10 or 10A may apply an estimate of epithelium thickness to perform functions such as:

Adjust the spatial frequencies of structured light patterns used for DOM (e.g. where the epithelium is determined to have a larger thickness at the location of probe 30 structured light patterns of longer wavelength (lower spatial frequencies) may be used to interrogate deeper into the epithelium while where the epithelium is determined to have a smaller thickness at the location of probe 30 the structured light patterns may be made to have higher spatial frequencies).

In cases where system 30 outputs an indication of tissue characterization the estimated epithelium thickness may be applied to adjust the tissue characterization. For example, in a case where the epithelium is thicker the tissue characterization may be adjusted toward normal (BS) whereas in a case where the epithelium is thin the tissue characterization may be adjusted toward a higher level of dysplasia.

In some embodiments instead of directly estimating the epithelium thickness, a system as described herein may accept user input identifying the nature of the tissue that probe 30 is applied to. For example, the user input may identify whether the tissue is tissue of the tongue, cheek, cervix, etc. Based on the user input the system may select appropriate structured illumination patterns and/or adjust tissue characterization algorithms as described above.

Controllers

Figure 12:
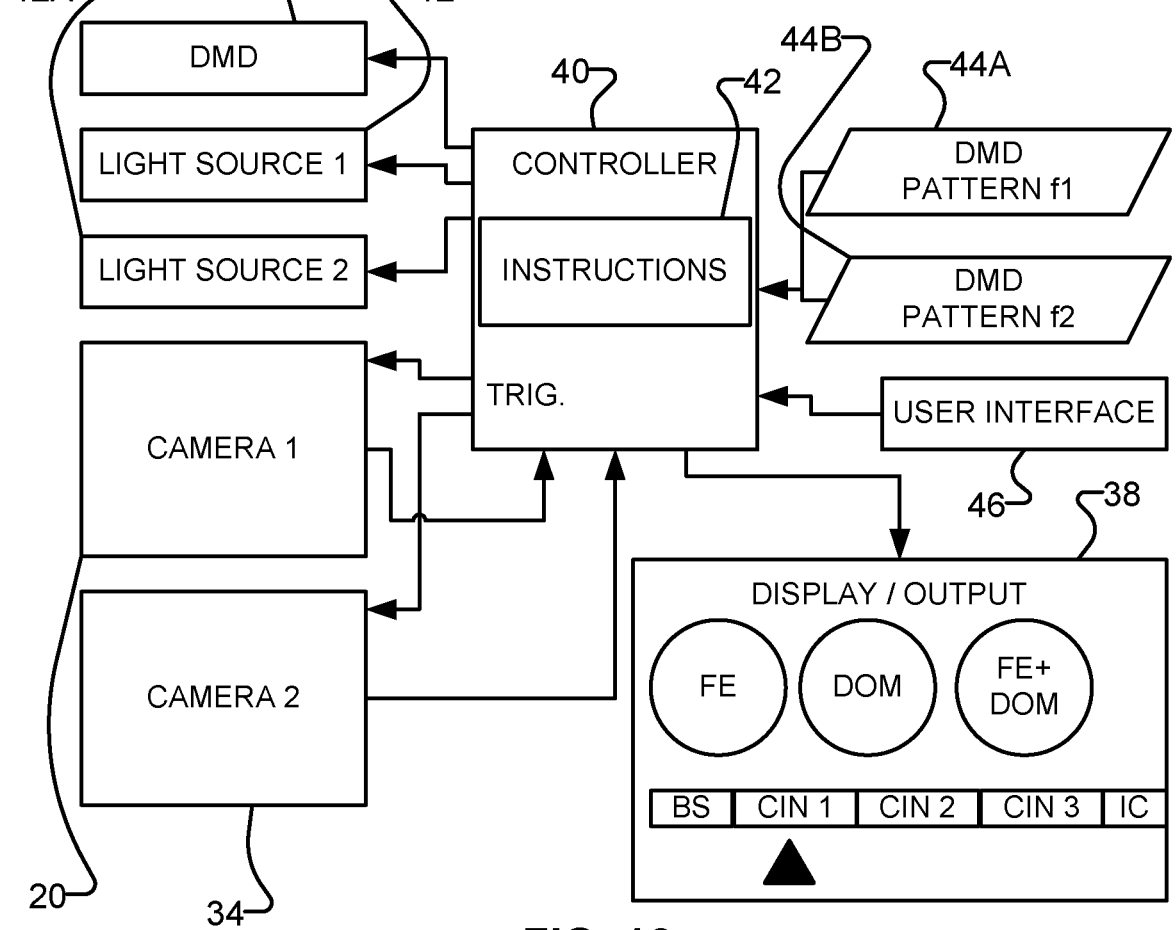
FIG. 12 is a block diagram of an example controller.

The complete combination of circuitry and data processing that regulates the operation of systems as described herein and/or handles and processes data generated by such systems to yield images, stored data, signals or other outputs may be called a controller, whether provided by a single localized device or plural devices that cooperate to provide the overall functioning of a system. FIG. 12 is a block diagram of an example controller 40.

Controller 40 comprises software instructions 42. Controller 40 may execute instructions 42 in order to control one or more components of system 10 or system 10A and/or to process images as described herein.

Controller 40 is connected to receive one or more inputs. These may include image data from cameras 20, 34, and/or 20A (not shown in FIG. 12). Inputs (e.g. desired settings or outputs) from a user interface 46 may also be sent to controller 40. User interface 46 may comprise, for example, a computer, a keyboard, a touch screen, a pointing device such as a mouse or trackball, a smartphone, a tablet computer, or the like.

In the illustrated embodiment controller 40 also has access to stored data representing structured light patterns to be generated. The data may, for example, comprise image data (e.g. patterns 44A and 44B as shown in FIG. 12). Patterns 44A and 44B may have different spatial frequencies. In other embodiments controller 40 may calculate structured light patterns on the fly.

Based on the inputs received by instructions 42, controller 40 may output commands to one or more components of system 10 or system 10A. For example, controller 40 may alter the setting of DMD 14A to select or change the spatial frequency or phase of a structured illumination pattern to be projected onto tissue T. Controller 40 may select the wavelength of light emitted by light source 12 and/or light source 12A, or turn light sources 12 and/or 12A on or off. Controller 40 may alter one or more settings of camera 20, camera 34, and/or camera 20A, or may operate or trigger camera 20 and/or camera 34 at the appropriate time to obtain the desired image(s) of tissue T.

Controller 40 may also perform processing of the images received from the connected cameras and control display 38. For example, controller 40 may cause display 38 to output an FE image, a DOM image, both FE and DOM images, or a composite DOM/FE image of tissue T. Controller 40 may also cause display 38 to output a classification of tissue T in any suitable form.

Some aspects of the invention can be embodied by controllers implemented by data processing systems that function to control cameras, spatial light modulators, light sources and other elements of systems as described herein and/or control or implement image processors in systems as described herein and/or in processing data from systems as described herein to provide images, signals, records, user feedback and other output. Such data processing systems may be implemented using specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and field programmable gate arrays ("FPGAs"). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a control circuit for a device may implement methods as described herein by executing software instructions in a program memory accessible to the processors.

Processing may be centralized or distributed. Where processing is distributed, information including software and/or data may be kept centrally or distributed. Such information may be exchanged between different functional units by way of a communications network, such as a Local Area Network (LAN), Wide Area Network (WAN), or the Internet, wired or wireless data links, electromagnetic signals, or other data communication channel(s).

Methods as described herein may be varied in ways that will be understood to those of skill in the art. While processes steps or blocks are presented in a given order, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times.

Certain aspects of the invention may also be provided in the form of a program product. The program product may comprise any non-transitory medium which carries a set of computer-readable instructions which, when executed by a data processor, cause the data processor to execute a method of the invention (e.g. a method of controlling a system as described herein to acquire FE and DOM images and/or to process image data and/or to generate output for a user). Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or preprogrammed chips (e.g., EEPROM semiconductor chips), nanotechnology memory, or the like. The computer-readable signals on the program product may optionally be compressed or encrypted.

Advantages

From the foregoing description it can be appreciated that various embodiments of the invention may offer some or all of the following advantages:

- systems as described herein may be designed in a way that makes them cost effective relative to other medical diagnostic equipment of a similar nature;
- the combined application of FE and DOM may yield more accurate tissue characterization;
- systems as described herein may be designed to make them effective for use as screening tools (for example, for screening lesions in the oral cavity, the cervix or other tissues);
- systems as described herein may provide real time feedback regarding the classification of tissues.

REFERENCES

The following references describe subject matter in the field of the invention. These references are hereby incorporated herein by reference for all purposes.

[1] M. Schiffman et al., "Human papillomavirus and cervical cancer," Lancet. 370: 890-907 (2007).
[2] http://globocan.iarc.fr/Pages/fact_sheets_cancer.aspx (Nov. 11, 2016)
[3] N. Bodenschatz et al., "Diffuse optical microscopy for quantification of depth-dependent epithelial backscattering in the cervix," J. Biomed. Opt. 21(6), 066001 (2016).
[4] N. Bozinovic et al., "Fluorescence endomicroscopy with structured illumination," Opt. Express 16(11), 8016-8025 (2008).
[5] C. Schlosser et al., "Fluorescence confocal endomicroscopy of the cervix: Pilot study on the potential and limitations for clinical implementation," submitted, J. Biomed. Opt. (2016).
[6] Redden Weber C, Schwartz R, Atkinson E N, Cox D D, MacAulay C, Follen M., Richards-Kortum R. Model-based analysis of reflectance and fluorescence spectra for in vivo detection of cervical dysplasia and cancer. J Biomed Opt. 13(6):064016, 2008.

Interpretation of Terms

Unless the context clearly requires otherwise, throughout the description and the claims:

- "comprise", "comprising", and the like are to be construed in an inclusive sense, as opposed to an exclusive or exhaustive sense; that is to say, in the sense of "including, but not limited to";
- "connected", "coupled", or any variant thereof, means any connection or coupling, either direct or indirect, between two or more elements; the coupling or connection between the elements can be physical, logical, or a combination thereof;
- "herein", "above", "below", and words of similar import, when used to describe this specification, shall refer to this specification as a whole, and not to any particular portions of this specification;

"or", in reference to a list of two or more items, covers all of the following interpretations of the word: any of the items in the list, all of the items in the list, and any combination of the items in the list;

the singular forms "a", "an", and "the" also include the meaning of any appropriate plural forms.

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Where a component (e.g. a lens, mirror, modulator, filter, camera, light source, software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

What is claimed is:

1. A system for combined diffuse optical microscopy (DOM) and fluorescence endomicroscopy (FE) comprising:
   a light source;
   a spatial light modulator illuminated by the light source and operative to spatially modulate the light from the light source to provide a structured illumination pattern;
   an optical system arranged to demagnify the structured illumination pattern and to direct the structured illumination pattern into a fiber bundle terminating at a probe tip;
   a first camera optically connected to receive light backscattered into the probe tip;
   a second camera optically connected to receive fluorescence light incident on the probe tip;
   a light filtering optical element in a light path between the probe tip and the second camera, the light filtering optical element operative to block light other than the fluorescence light;
   a controller comprising an image processing system connected to receive image data from the first camera and the second camera and to process the image data to yield a DOM image based on images from the first camera and a FE image based on images from the second camera, the FE image coregistered with the DOM image.

2. The system according to claim 1 wherein the light source comprises a blue light source.

3. The system according to claim 1 wherein the light filtering optical element passes optical radiation having wavelengths corresponding to fluorescent emissions of acriflavine hydrochloride (AH).

4. The system according to claim 1 wherein the structured light pattern is spatially periodic with a spatial frequency in at least one direction and the controller is operative to control the spatial light modulator to modulate the light from the light source according to the structured light pattern and to trigger the first and second cameras to capture images while the spatial light modulator is modulating the light from the light source according to the structured light pattern.

5. The system according to claim 4 wherein the controller is operative to apply phase shifts to the structured light pattern in the at least one direction and to, in a sequence, control the spatial light modulator to modulate the light from the light source according to the structured light pattern with different phase shifts applied, and to trigger the first and second cameras to capture images while the spatial light modulator is modulating the light from the light source according to the structured light pattern with each of the applied phase shifts.

6. The system according to claim 4 wherein the controller is operative to alter the spatial frequency of the structured light pattern and to control the spatial light modulator to modulate the light from the light source according to the structured light pattern with one of plural different spatial frequencies, and to trigger the first and second cameras to capture images while the spatial light modulator is modulating the light from the light source according to the structured light pattern with each of the plural spatial frequencies.

7. The system according to claim 6 wherein, for each of the plural spatial frequencies, the controller is operative to apply phase shifts to the structured light pattern in the at least one direction and to, in a sequence, control the spatial light modulator to modulate the light from the light source according to the structured light pattern with different phase shifts applied, and to trigger the first and second cameras to capture images while the spatial light modulator is modulating the light from the light source according to the structured light pattern with each of the applied phase shifts.

8. The system according to claim 6 wherein the controller is configured to determine a ratio (R) of images from the first camera corresponding to different ones of the plural spatial frequencies.

9. The system according to claim 5 wherein the system is configured to combine captured images for each of the phase shifts.

10. The system according to claim 9 wherein, in combining the captured images for each of the phase shifts, the system computes differences between pairs of the captured images and sums the differences wherein, in combining the captured images the system computes the value $$R = A\sqrt{(X_1-X_2)^2+(X_2-X_3)^2+(X_3-X_1)^2}$$

where $X_1$, $X_2$ and $X_3$ are captured images for three different phase shifts and A is a constant.

11. The system according to claim 9 wherein, in combining the captured images from the first camera, the system is configured to, for each of the phase shifts, compute differences between pairs of the captured images and sum the resulting differences and, in combining the captured images from the second camera, the system is configured to average the captured images.

12. The system according to claim 1 wherein the controller is configured to process the images from the second camera to calculate a measure of nuclear-to-cytoplasmic ratio.

13. The system according to claim 8 wherein the controller is configured to process the images from the second camera to calculate a measure of nuclear-to-cytoplasmic ratio (NCR) and to characterize tissues imaged by the system based on a discriminant function having the NCR and R as inputs.

14. The system according to claim 1 wherein the controller is configured to control the spatial modulation provided by the spatial light modulator to project structured illumination having plural different spatial frequencies, control the first camera to capture one or more images corresponding to the structured illumination of each of the plural spatial frequencies, and process the captured images to calculate a ratio of reflectance for one or more pairs of the plural spatial frequencies.

15. The system according to claim 14 wherein the controller is configured to calculate the ratio of reflectance on a pixel-by pixel basis and generate a pseudo colour image with colour set according to the ratio of reflectance.

16. The system according to claim 1 wherein the controller is configured to control the spatial modulation provided by the spatial light modulator to project structured illumination having plural different spatial frequencies, control the first camera to capture one or more images corresponding to the structured illumination of each of the plural spatial frequencies, and process the captured images to generate a combined pseudo colour image wherein different colour channels of the pseudo colour image are respectively set based on captured images corresponding to different ones of the plural spatial frequencies such that changes with position in ratios of the reflectance corresponding to different spatial frequencies correspond to colour shifts in the pseudo colour image.

17. The system according to claim 1 wherein the first camera is a multi-spectral camera and the controller is configured to control the spatial modulation provided by the spatial light modulator to project structured illumination having one or more spatial frequencies, control the first camera to capture one or more images corresponding to the structured illumination and process the captured images to generate a pseudo colour image wherein different colour channels of the pseudo colour image are respectively set based on different spectral channels of the multispectral first camera.

18. The system according to claim 1 wherein the first camera is a multispectral camera, the controller is configured to control the spatial modulation provided by the spatial light modulator to project structured illumination having plural different spatial frequencies, control the first camera to capture one or more images corresponding to the structured illumination of each of the plural spatial frequencies, and process the captured images to generate a combined pseudo colour image wherein different colour channels of the pseudo colour image are respectively set based on captured images corresponding to different ones of the plural spatial frequencies and/or different spectral channels of the multispectral camera such that changes with position in ratios of the reflectance corresponding to different spatial frequencies and/or different spectral channels correspond to colour shifts in the pseudo colour image.

19. The system according to claim 1 wherein the controller is configured to determine a depth of an epithelial tissue adjacent to the probe tip and to control the spatial modulation provided by the spatial light modulator based at least in part on the depth.

* * * * *